US011234945B2

(12) United States Patent
Vardy et al.

(10) Patent No.: US 11,234,945 B2
(45) Date of Patent: Feb. 1, 2022

(54) WOUND HEALING COMPOSITION

(71) Applicant: AGENCY FOR SCIENCE, TECHNOLOGY AND RESEARCH, Singapore (SG)

(72) Inventors: Leah Vardy, Singapore (SG); Hui Kheng Lim, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/314,380

(22) PCT Filed: Jul. 3, 2017

(86) PCT No.: PCT/SG2017/050336
§ 371 (c)(1),
(2) Date: Dec. 28, 2018

(87) PCT Pub. No.: WO2018/004467
PCT Pub. Date: Jan. 4, 2018

(65) Prior Publication Data
US 2019/0262282 A1    Aug. 29, 2019

(30) Foreign Application Priority Data
Jul. 1, 2016   (SG) ........................... 10201605436U

(51) Int. Cl.
*A61K 31/132*     (2006.01)
*A61P 17/02*     (2006.01)
(Continued)

(52) U.S. Cl.
CPC .......... *A61K 31/132* (2013.01); *A61K 31/198* (2013.01); *A61K 31/7076* (2013.01); *A61K 31/713* (2013.01); *A61P 17/02* (2018.01)

(58) Field of Classification Search
CPC .............. A61K 2300/00; A61K 31/132; A61K 31/198; A61K 31/7076; A61K 31/7105; A61K 31/713; A61P 17/02
See application file for complete search history.

(56) References Cited

U.S. PATENT DOCUMENTS

2002/0045780 A1    4/2002   Bergeron, Jr.

FOREIGN PATENT DOCUMENTS

EP         0248217 A2    12/1987
WO     1996/33703 A2    10/1996
(Continued)

OTHER PUBLICATIONS

Wang et al. (Abstract, American Journal of physiology 1990, 259, (4, Pt. 1) (Year: 1990).*
(Continued)

*Primary Examiner* — Savitha M Rao
(74) *Attorney, Agent, or Firm* — Womble Bond Dickinson (US) LLP

(57) ABSTRACT

Disclosed herein are pharmaceutical compositions comprising at least one polycationic aliphatic amine, in particular spermidine, spermine or a combination thereof. The compositions can further comprise one or more selected from decarboxylated S-adenosylmethionine and an inhibitor of ornithine decarboxylase 1 (ODC1) such as difluoromethyl ornithine (DFMO). Also disclosed herein are methods of determining the presence of a type of wound and methods for treating the same, i.e. acute or non-healing wounds, which in a particular embodiment, comprises determining the ratio of putrescine versus spermidine/spermine. The present disclosure also includes methods promoting re-epithelialisation of wounds and pharmaceutical compositions for the same use.

7 Claims, 20 Drawing Sheets

Specification includes a Sequence Listing.

(51) Int. Cl.
A61K 31/198 (2006.01)
A61K 31/7076 (2006.01)
A61K 31/713 (2006.01)

(56) References Cited

FOREIGN PATENT DOCUMENTS

| | | | |
|---|---|---|---|
| WO | 1997/11691 | A1 | 4/1997 |
| WO | 2003/013245 | A1 | 2/2003 |
| WO | 2003/057172 | A2 | 7/2003 |
| WO | 2011/113005 | A2 | 9/2011 |
| WO | 2014/167003 | A1 | 10/2014 |

OTHER PUBLICATIONS

Nagoshi et al. (Abstract, Biochimica et Biophysica Acta, General Subjects (2003), 1619(2), 187-192 (Year: 2003).*
Sams-Dodd (Drug discovery today, vol. 10, No. 2, 2005, pp. 139-147 ) (Year: 2005).*
Schafer et al. Drug Discovery Today 2008, 13 (21/22), 913-916 (Year: 2008).*
Horig et al. Journal of Translational Medicine 2004, 2(44) (Year: 2004).*
The Extended European Search Report for European Application No. 17820676.9 dated Jan. 27, 2020, 8 pages.
The Written Opinion for Singapore Application No. 11201811755P dated Apr. 6, 2020, 8 pages.
Lowe et al., "Cutaneous polyamines in psoriasis", British Journal of Dermatology, Sep. 20, 1981, 5 pages.
Anthony E. Pegg, "Functions of Polyamines in Mammals", The Journal of Biological Chemistry, Jun. 7, 2016, 10 pages.
Leopold et al., "A comparison of epithelial-to-mesenchymal transition and reepithelialization", Seminars in Cancer Biology, Jul. 31, 2012, vol. 22, No. 5-6, pp. 471-483.
Broshtilova et al., "Comparative analysis of polyamine metabolism in benign and neoplastic keratinocyte proliferations," Acta Dermatovenerol Alp Pannonica Adriat., Feb. 19, 2012, vol. 21, No. 1, pp. 3-5.
Chen et al., "Effects of different concentrations of putrescine on proliferation, migration and apoptosis of human skin fibroblasts," J South Med Univ., May 27, 2015, vol. 35, No. 5, pp. 758-762.
Igarashi et al., "Formation of a Compensatory Polyamine by Escherichia coli Polyamine-Requiring Mutants during Growth in the Absence of Polyamines," J. Bacteriology, Apr. 1986, vol. 166, No. 1, pp. 128-134.
International Search Report and the Written Opinion of the International Searching Authority for International Application No. PCT/SG2017/050336 dated Sep. 25, 2017.
Casero, et al., "Targeting polyamine metabolism and function in cancer and other hyperproliferative diseases," Nature Reviews: Drug Discovery, May 2007, pp. 373-390, vol. 6, Nature Publishing Group.
Casero, et al., "Polyamine catabolism and disease," Biochem J., Aug. 1, 2010, pp. 323-338, vol. 421, No. 3, National Institutes of Health.
Cordeiro, et al., "The role of transcription-independent damage signals in the initiation of epithelial wound healing," Nature Reviews: Molecular Cell Biology, Apr. 2013, pp. 249-262, vol. 14, Macmillan Publishers Limited.
Dickson, et al., "Human Keratinocytes That Express hTERT and Also Bypass a p16ink4a-Enforced Mechanism That Limits Life Span Become Immortal yet Retain Normal Growth and Differentiation Characteristics," Molecular and Cellular Biology, Feb. 2000, pp. 1436-1447, vol. 20, No. 4, American Society for Microbiology.
Donati, et al., "Stem Cell Heterogeneity and Plasticity in Epithelia," Cell Stem Cell Review, May 7, 2015, pp. 465-476, vol. 16, Elsevier Inc.
Eisenberg, et al., "induction of autophagy by spermidine promotes longevity," Nature Cell Biology, Nov. 2009, pp. 1305-1337, vol. 11, No. 11 Macmillan Publishers Limited.
El Baze, et al., "Polyamine Levels in Normal Human Skin," Archive of Dermatological Research, 1983, pp. 218-221, vol. 275, Springer-Verlag 1983.
Gao, et al., "Roles of Cellular Polyamines in Mucosal Healing in the Gastrointestinal Tract," Journal of Physiology and Pharmacology, 2013, pp. 681-693, vol. 64, No. 6.
Gilad, et al., "Overview of the Brain Polyamine-Stress-Response: Regulation, Development, and Modulation by Lithium and Role in Cell Survival," Cellular and Molecular Neurobiology, Oct. 2003, pp. 1-13, vol. 23, Nos. 4/5, Plenum Publishing Corporation.
Hitamatsu, et al., "Alterations in Polyamine Levels in Amniotic Fluid, Plasma and Urine During Normal Pregnancy," Acta Medica Okayama, Oct. 1985, pp. 339-346, vol. 39, No. 5, Okayama University Medical School.
Hurd, et al., "Redox regulation of cell migration and adhesion," Trends Cell Biol, Feb. 2012, pp. 107-115, vol. 22, No. 2, HHS Public Access.
Igarashi, et al., "Modulation of cellular function by polyamines," The International Journal of Biochemistry & Cell Biology, 2010, pp. 39-51, vol. 42, Elsevier.
Igarashi, et al., "Modulation of Protein Synthesis by Polyamines," Critical Review, Mar. 2015, pp. 160-169, vol. 67, No. 3, IUBMB LIFE.
Keledjian, et al., "Induced PDK1 kinase activity suppresses apoptosis in intestinal epithelial cells by activating Akt signaling following polyamine depletion," Int J Clin Exp Med, 2012, pp. 221-228, vol. 5, No. 3, Baltimore, Maryland.
Lightfoot, et al.,"Endogenous polyamine function—the RNA perspective," Nucleic Acids Research, Sep. 17, 2014, p. 11275-11290, vol. 42, No. 18, The Author(s).
Maeno, et al., "A Study on the Vital Reaction in Wounded Skin: Simultaneous Determination of Histamine and Polyamines in injured Rat Skin by High-Performance Liquid Chromatography," Forensic Science International, 1990, pp. 255-268, vol. 46, Elsevier Scientific Publishers Ireland Ltd.
Martin, et al., "Wound healing in zebrafish," Nature: Inflammation, Jun. 18, 2009, pp. 921-923, vol. 459, Macmillan Publishers Limited.
Minois, et al., "Polyamines in aging and disease," Aging, Aug. 2011, pp. 1-17, vol. 3, No. 8, www.ImpactAging.com.
Mizutani, et al., "Changes in Polyamine Metabolism During Wound Healing in Rat Skin," Biochimica et Biophysica Acta, 1974, pp. 183-190, vol. 338, Elsevier Scientific Publishing Company, Amsterdam.
Moreria, et al., "Prioritization of Competing Damage and Development Signals by Migrating Macrophages in the Drosophila Embryo," Current Biology, Mar. 9, 2010, pp. 464-470, vol. 20, No. 5, Elsevier Ltd.
Niethammer, et al., "A tissue-scale gradient of hydrogen peroxide mediates rapid wound detection in zebrafish," Nature, Jun. 18, 2009, pp. 996-999, vol. 459, No. 7249, HHS Public Access.
Nowotarski, et al., "Polyamines and cancer: Implications for chemoprevention and chemotherapy," Expert. Rev Mol Med, May 20, 2014, pp. 1-28, vol. 15, NIH Public Access.
Pastar, et al., "Epithelialization in Wound Healing: A Comprehensive Review," Advances in Wound Care, 2014, pp. 445-464, vol. 3, No. 7, Mary Ann Liebert, In.
Pegg, et al., "S-Adenosylmethionine decarboxylase," Essays Biochem, 2009, pp. 25-45, vol. 46, The Authors Journal Compilation and Biochemical Society.
Pegg, et al., "Mammalian Polyamine Metabolism and Function," IUBMB Life, Sep. 2009, pp. 880-894, vol. 61, No. 9, NIH Public Access.
Perez-Leal, et al., "Regulation of polyamine metabolism by translational control," Amino Acids, 2012, pp. 611-617, vol. 42, Springer.
Pucciarelli, et al., "Spermidine and Spermine are Enriched in Whole Blood of Nona/Centenarians," Rejuvenation Research, 2012, vol. 15, No. 6, Mary Ann Liebert, Inc.

(56) References Cited

OTHER PUBLICATIONS

Rao, et al., "Polyamines regulate intestinal epithelial restitution through TRPC1-mediated Ca2+ signaling by differentially modulating STIM1 and STIM2," Am J Physiol Cell Physiol, 2012, pp. C308-C317, vol. 303.

Razzell, et al., "Calcium Flashes Orchestrate the Wound Inflammatory Response through DUOX Activation and Hydrogen Peroxide Release," Current Biology, Mar. 4, 2013, pp. 424-429, vol. 23, Elsevier.

Rheinwald, et al., "A Two-Stage, p16ink4a- and p53-Dependent Keratinocyte Senescence Mechanism That Limits Replicative Potential Independent of Telomere Status," Molecular and Cellular Biology, Jul. 2002, pp. 5157-5172, vol. 22, No. 14, American Society for Microbiology.

Saito, H., "Alterations of Polyamines in Body Fluids During Pregnancy in Rats," Acta Obst Gynaec Jpn, Feb. 1985, pp. 293-300, vol. 37, No. 2, Japan Society of Obstetrics and Gynecology.

Sasaki, et al., "Generation of a multi-layer muscle fiber sheet from mouse ES cells by the spermine action at specific timing and concentration," Differentiation, 2008, pp. 1023-1030, vol. 76, The Authors.

Schimohowitsch, et al., "Polyamine and aminoguanidine treatments to promote structural and functional recovery in the adult mammalian brain afte injury: A brief literature review and preliminary data about their combined administration," Journal of Physiology, 2006, pp. 221-231, vol. 99, Paris, France.

Shaw, et al., "Wound repair: a showcase for cell plasticity and migration," Current Opinion in Cell Biology, 2016, pp. 29-37, vol. 42, Science Direct, Elsevier.

Shi, et al., "Effect of Supplemental Ornithine on Wound Healing," Journal of Surgical Research, 2002, pp. 299-302, vol. 106, Elsevier Science.

Smith, et al., "Regulation of cell signalling by uPAR," Nature Reviews: Molecular Cell Biology, Jan. 2010, pp. 23-36, vol. 11, Macmillan Publishers Limited.

Telorack, et al., "A Glutathione-Nrf2-Thioredoxin Cross-Talk Ensures Keratinocyte Survival and Efficient Wound Repair," PLOS Genetics, Jan. 25, 2016, pp. 1-27, vol. 12, No. 1.

Tran, et al., "A Wound-induced [CA2+] Increase and Its Transcriptional Activation of Immediate Early Genes Is Important in the Regulation of Motility," Experimental Cell Research, 1999, pp. 319-326, vol. 246, Academic Press.

Veal, et al., "Hydrogen Peroxide as a Signaling Molecule," Antioxidants & Redox Signaling, 2011, pp. 147-152, vol. 15, No. 1, Mary Ann Liebert, Inc.

Wang, et al., "Polyamines and Ornithine Decarboxylase During Repair of Duodenal Mucosa After Stress in Rats," Gastroenterology, 1991, pp. 333-343, vol. 100, The American Gastroenterological Association.

Wang, et al., "Luminal Polyamines Substitute for Tissue Polyamines in Duodenal Mucosal Repair After Stress in Rats," Gastroenterology, 1992, pp. 1109-1117, vol. 102, The American Gastroenterological Association.

Wang, et al., "Luminal polyamines stimulate repair of gastric mucosal stress ulcers," The American Physiological Society, 1990, 9 pgs., The American Physiological Society.

Yan, et al., "Epithelial to Mesenchymal Transition in Human Skin Wound Healing is Induced by Tumor Necrosis Factor-$\alpha$ through Bone Morphogenic Protein-2," The American Journal of Pathology, May 2010, pp. 2247-2258, vol. 176, No. 5, American Society for Investigative Pathology.

Yu, et al., "Chk2-dependent HuR phosphorylation regulates occludin mRNA translation and peithelial barrier function," Nucleic Acids Research, 2011, pp. 8472-8487, vol. 39, No. 19, The Authors.

Zhang, et al., "AMD1 is essential for ESC self-renewal and is translationally down-regulated on differentiation to neural precursor cells," Genes & Development, 2012, pp. 461-473, vol. 26, Cold Spring Harbor Laboratory Press ISSN 0890-9369/12.

Zhao, et al., "A role for polyamine regulators in ESC self-renewal," Cell Cycle, Dec. 15, 2012, pp. 4517-4523, vol. 11, No. 24, Landes Bioscience.

Zou, et al., "Polyamines Regulate the Stability of JunD mRNA by Modulating the Competitive Binding of Its 3' Untranslated Region to HuR and AUF1," Molecular and Cellular Biology, 2010, pp. 5021-5032, vol. 30, No. 21, American Society for Microbiology.

The International Preliminary Report on Patentability for counterpart PCT Application No. PCT/SG2017/050336 dated Jan. 1, 2019, 8 pages.

\* cited by examiner d e f g c continued

WOUND HEALING COMPOSITION

CROSS-REFERENCE TO RELATED APPLICATIONS

This patent application is a U.S. National Phase Application Under 35 U.S.C. § 371 of International Application No. PCT/SG2017/050336, filed on 3 Jul. 2017, entitled A WOUND HEALING COMPOSITION, which claims the benefit of priority of Singapore provisional application No. 10201605436U, filed 1 Jul. 2016, the contents of which were incorporated by reference in the entirety for all purposes.

INCORPORATION BY REFERENCE

This patent application incorporates by reference the material (i.e., Sequence Listing) in ASCII text file named 9869SG5358_Seq_listing_ST25_5298609_1.txt, created 12 Apr. 2019, having a file size of 1,114 bytes.

FIELD OF THE INVENTION

The present invention relates generally to the field of molecular biology. In particular, the present invention relates to the use of polyamines in the detection and treatment of wounds.

BACKGROUND OF THE INVENTION

It is estimated that over 400 million people globally have diabetes (http://www.idf.org). Singapore has the second highest incidence second only to the United States, and the numbers are set to rise significantly. A major complication of diabetes is non-healing wounds and it is estimated that 33% of the annual diabetes budget is spent on diabetic foot ulcers. The inability to diagnose non-healing wounds early or effectively treat them has resulted in dramatically increased wound care costs in Singapore in recent years, with current estimates being well over S$700 million annually.

Recently, there has been a startling rise in the number of wounds that do not heal. What can start as a small scratch, can later become a large, non-healing wound that in some cases can only be treated with limb amputation. The rise in non-healing wounds is closely linked to the dramatic increase in the incidence of diabetes, vascular disease and the aging population. In Singapore alone it is estimated that 11% of 20-80 year olds have diabetes, second only to the United States. This number is set to rise significantly. Non-healing wounds or ulcers can persist for 12 months or longer and have a very high recurrence rate of 65%. The care of non-healing wounds is estimated to cost between 2 and 3% of the annual healthcare budget. Despite their prevalence and the significant healthcare burden of non-healing wounds, there remains no effective treatment. In Singapore, non-healing wounds are the leading cause of non-traumatic lower limb amputations with more than 4 lower limb amputations-due to diabetic foot ulcers-occurring daily.

Thus there is an unmet need for providing compositions and methods for treating non-healing wounds.

SUMMARY OF THE INVENTION

In one aspect, the present invention refers to a pharmaceutical composition comprising at least one polycationic aliphatic amine, wherein the polycationic aliphatic amine has at least 3 or more amino groups, of which two amino groups are terminal amino groups; wherein the pharmaceutical composition further comprises any one or more selected from the group consisting of decarboxylated S-adenosylmethionine (S-adenosylmethioninamine or AdometDC or dcAdoMet) and an inhibitor of ornithine decarboxylase 1 (ODC1).

In another aspect, the present invention refers to a method of promoting re-epithelialisation of a wound, the method comprising administering a pharmaceutically effective amount of a composition disclosed herein to a subject in need thereof.

In yet another aspect, the present invention refers to a method of treating a wound, the method comprising administering a pharmaceutically effective amount of a composition as disclosed herein to a subject in need thereof.

In a further aspect, the present invention refers to a method of determining whether a subject is suffering from an acute or non-healing wound, the method comprising determining the level of at least one polycationic aliphatic amine in a sample obtained from the wound of the subject; comparing the levels of the at least one polycationic aliphatic amine with the levels of the same polycationic aliphatic amine found in a sample obtained from a subject without wound; wherein, upon comparison, an increased level of the at least one polycationic aliphatic amine in the wound sample is indicative of a non-healing environment; wherein the polycationic aliphatic amine(s) has at least 2 or more amino groups of which 2 amino groups are terminal amino groups.

In another aspect, the present invention refers to A method of determining progression of wound healing of a subject suffering from a wound, the method comprising determining the level of at least one polycationic aliphatic amine in a sample obtained from the wound of the subject; comparing the levels of the at least one polycationic aliphatic amine with the levels of the same polycationic aliphatic amine found in a sample obtained from a subject without wound; wherein, upon comparison, a decreased level of the at least one polycationic aliphatic amine in the wound sample compared to the level of the same polycationic aliphatic amine in the sample obtained from a subject without wound is indicative of progression of wound healing, wherein an increased level of the at least one polycationic aliphatic amine in the wound sample compared to the level of the same polycationic aliphatic amine in the sample obtained from a subject without wound is indicative of no progression or regression of wound healing; wherein the polycationic aliphatic amine(s) has at least 2 or more amino groups In yet another aspect, the present invention refers to use of the pharmaceutical composition as defined herein in the manufacture of a medicament for treating a wound.

In a further aspect, the present invention refers to use of the pharmaceutical composition as defined herein in the manufacture of a medicament for promoting re-epithelialisation of a wound.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
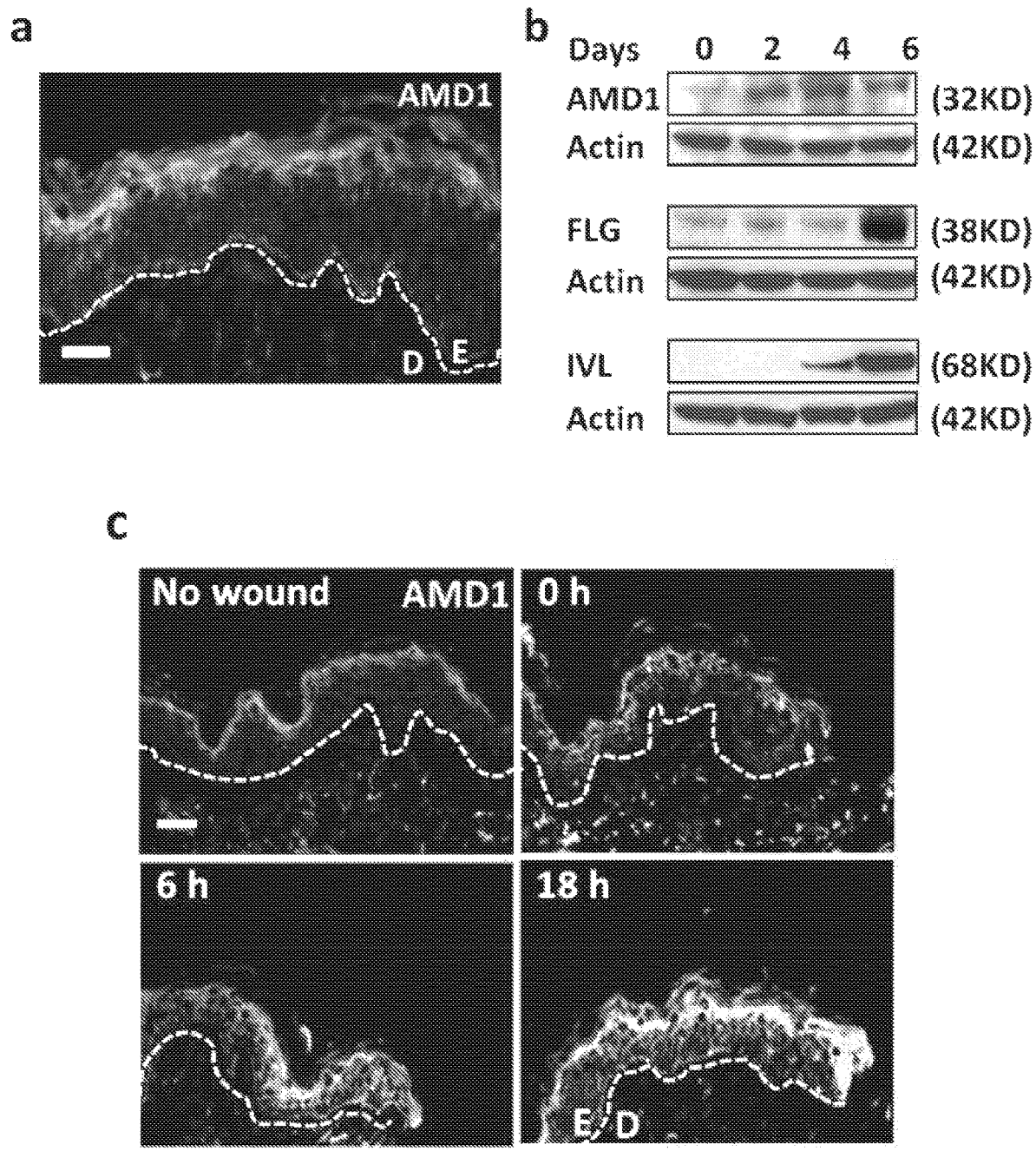
FIG. 1 depicts data showing that AMD1 is upregulated in wound-edge keratinocytes. (a) Immunofluorescence of AMD1 expression in skin biopsies from healthy donors (n=3) counterstained with Hoechst (DNA). Scale bar=25 µm. AMD1 is expressed in the more differentiated layers of the skin epidermis. (b) Detection of AMD1 and epidermal differentiation markers (FLG: filaggrin and IVL: involucrin) by western blot following induction of keratinocytes differentiation with 1.2 mM calcium for 0, 2, 4, and 6 days. (c,d) Immunofluorescence staining of AMD1 in (c) human wound sections (n=3), scale bar=25 μm, and (d) scratched keratinocyte monolayer. Scale bar=100 μm. Hoechst DNA staining is shown. (e,f) Increased expression of AMD1 and ODC1 observed in scratched keratinocytes by western blot and RT-PCR. No observable change detected in SMS expression. (g) Immunofluorescence staining of ODC1 in scratched keratinocyte monolayer, Hoechst DNA staining is shown. Scale bar=50 μm. NS denotes no scratch; E denotes epidermis; D denotes dermis. Mean±standard error of three sets of independent experiments are shown. *$P \leq 0.05$, $P \leq 0.01$, and *$P \leq 0.001$.
Figure 1:
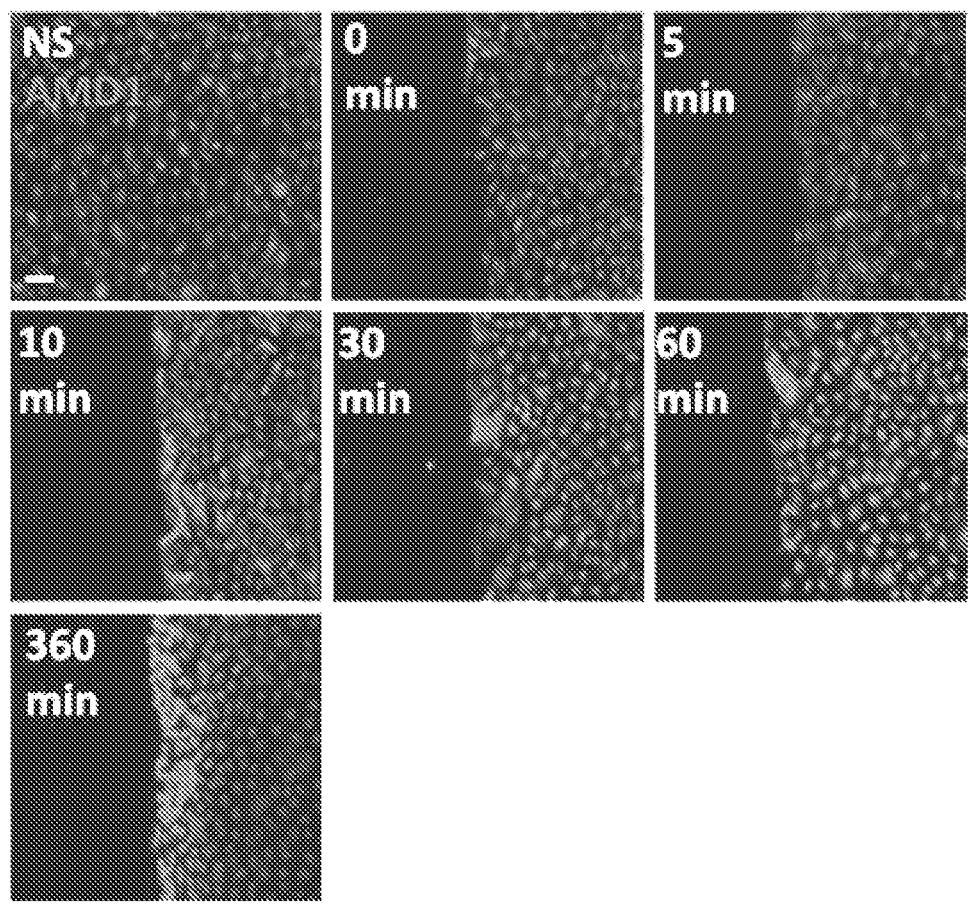
Figure 1:
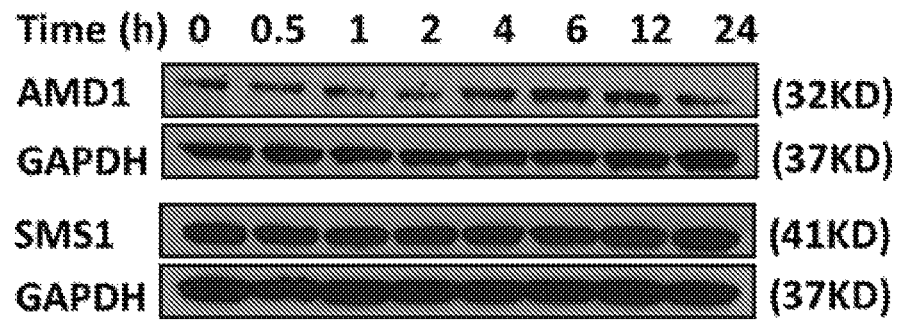
Figure 1:
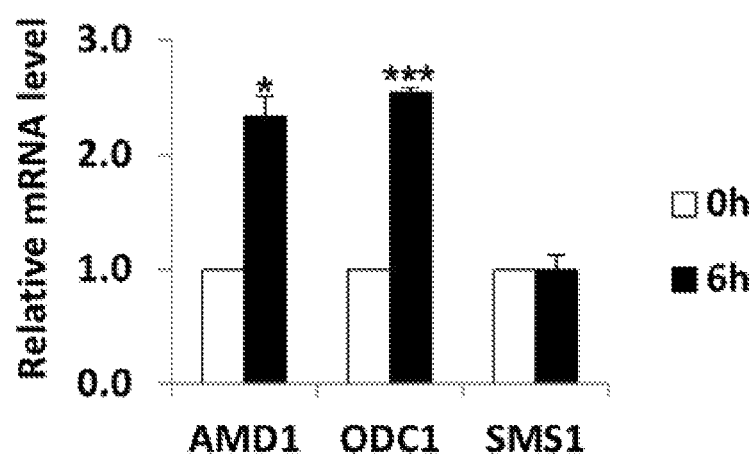
Figure 1:
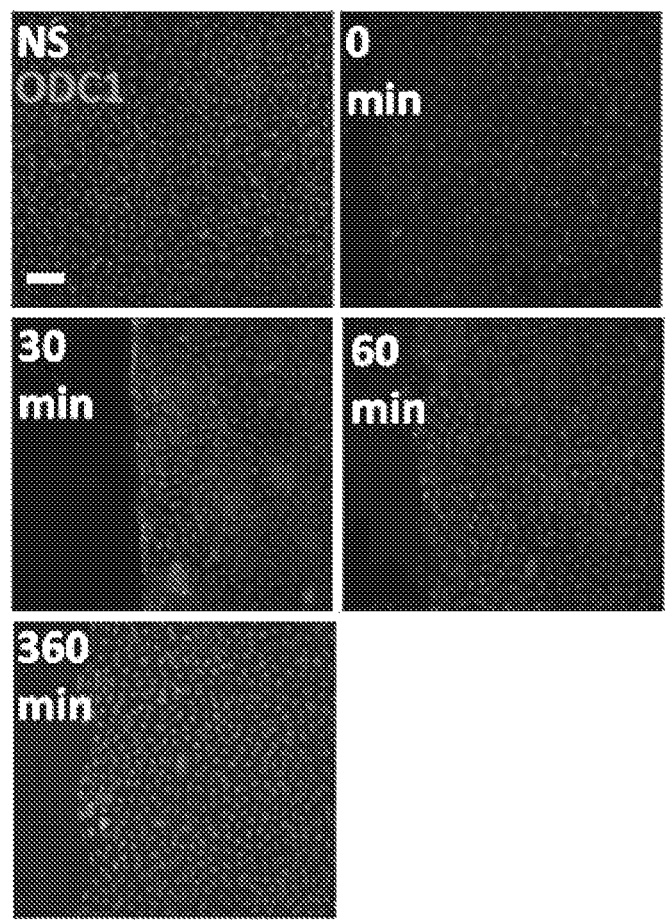

The skin has an incredible ability to heal itself following wounding, and it is this rapid response that is essential for preventing infection and maintaining a barrier function. Upon wounding, an elaborate and tightly orchestrated response occurs within seconds, resulting in wound closure within a few days. There has been a rise in the number of wounds that do not heal. What can start as a small scratch may later become a large, non-healing wound that, in some cases, can only be treated with limb amputation.

The rise in non-healing wounds is closely linked to the dramatic increase in the incidence of diabetes, vascular disease and the ageing population. In Singapore alone it is estimated that 11% of 20-80 year olds have diabetes, second only to the United States. This number is set to rise significantly.

Non-healing wounds or ulcers can persist for 12 months or longer and have a very high recurrence rate of 65%. The care of non-healing wounds is estimated to cost between 2 and 3% of the annual healthcare budget. Despite their prevalence and the significant healthcare burden of non-healing wounds, there remains no effective treatment. In Singapore, non-healing wounds are the leading cause of non-traumatic lower limb amputations, with more than 4 lower limb amputations, for example, due to diabetic foot ulcers, occurring daily.

Critical to developing therapies and diagnostics for detecting and treating non-healing wounds is an understanding of the pathophysiology behind them. This can only be achieved by understanding the normal process of wound healing to be able to determine the causes for non-healing wounds.

The process of wound healing is an elaborate and regulated sequence of events involving a multitude of different cell types and signalling pathways. Upon wounding, inflammatory cells are recruited to protect against infection. A fibrin clot is formed to seal the wound until a new skin barrier can be constructed. Fibroblasts migrate to the wound bed and form granulation tissue. Activated keratinocytes at the wound edge migrate across the wound bed until the epithelial tongues meet at the wound centre. From here, keratinocytes differentiate to form a new skin barrier. On epidermal wounding, keratinocytes at the wound edge undergo a transition from a non-motile epithelial state to a mesenchymal-like state, where they lose cell-cell contacts and become motile. Migrating cells reorganize their actin cytoskeleton and secrete proteases to remodel the extracellular matrix (ECM) and enable migration across the wound. Directly behind the migrating cells, keratinocytes rapidly proliferate to provide enough cells to cover the wound. Non-healing wounds are characterised by defective fibroblast and keratinocyte migration, where, as a result, re-epithelialization fails to occur.

It has been shown in the present application that one of the key players in wound healing are the polyamines putrescine, spermidine and spermine. The diamine, putrescine, and the higher order polyamines, spermidine and spermine, are naturally occurring cations present in all cells, and are essential for proliferation and a wide range of cellular events.

Figure 7:
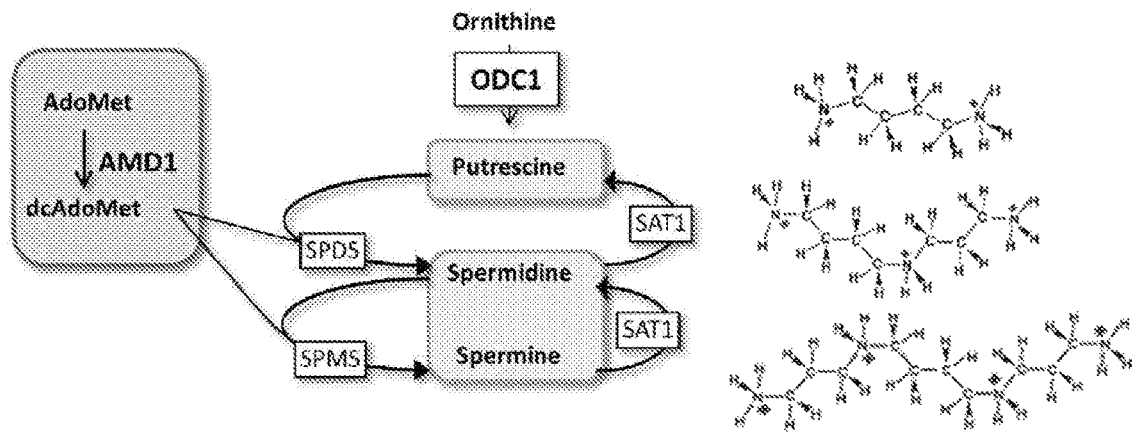
FIG. 7 shows a schematic diagram of an overview of the polyamine pathway.

Putrescine is synthesized within cells by decarboxylation of ornithine by the rate-limiting enzyme, ODC1. Putrescine is then sequentially converted into spermidine and spermine by the addition of an aminopropyl group from dcAdoMet. dcAdoMet is generated by the decarboxylation of AdoMet by AMD1, a second rate-limiting enzyme in the polyamine pathway. The levels and activity of ODC1 and AMD1 thus directly influence the levels and ratios of the three polyamines produced (FIG. 7).

Based on these findings, the present invention refers to a pharmaceutical composition comprising at least one polycationic aliphatic amine. The polycationic aliphatic amine has at least 3 or more amino groups, of which two amino groups are terminal amino groups. In another example, the pharmaceutical composition further comprises either decarboxylated S-adenosylmethionine (S-adenosylmethioninamine or AdometDC or dcAdoMet) or an inhibitor of ornithine decarboxylase 1 (ODC1), or both. In yet another example, the pharmaceutical composition further comprises either decarboxylated S-adenosylmethionine (S-adenosylmethioninamine or AdometDC or dcAdoMet). In a further example, the pharmaceutical composition further comprises an inhibitor of ornithine decarboxylase 1 (ODC1). In another example, the pharmaceutical composition further comprises decarboxylated S-adenosylmethionine (S-adenosylmethioninamine or AdometDC or dcAdoMet) and an inhibitor of ornithine decarboxylase 1 (ODC1). In another example, the pharmaceutical composition comprises any one of the following combinations: A) an ODC1 inhibitor combined with spermine; B) an ODC1 inhibitor combined with spermidine; C) decarboxylated S-adenosylmethionine combined with spermine; D) decarboxylated S-adenosylmethionine combined with spermidine; E) an ODC1 inhibitor combined with spermine and spermidine; F) decarboxylated S-adenosylmethionine combined with spermine and spermidine; or G) an ODC1 inhibitor combined with decarboxylated S-adenosylmethionine, spermidine and spermine.

As used herein, the term "polycationic aliphatic amine" refers to an open chained organic compound, comprising an amine group and one or more positive charges. Thus, in one example, the polycationic aliphatic amine is a polyamine. In another example, the polycationic aliphatic amine comprises at least 3, at least 4, at least 5 or at least 6 amino groups. In another example, the polycationic aliphatic amine comprises at least 4, at least 5 or at least 6 amino groups. In one example, the polycationic aliphatic amine comprises 3, 4, 5 or 6 amino groups.

In one example, at least one of the amino groups of the polycationic aliphatic amine is a secondary amino group.

In another example, the polycationic aliphatic amine is spermidine, spermine or a combination thereof. When referring to more than one polycationic aliphatic amine, in one example, the first polycationic aliphatic amine is putrescine (butane-1,4-diamine). In another example, the second polycationic aliphatic amine is spermidine (1,4-butanediamine, N-(3-aminopropyl)), spermine (1,4-butanediamine, N,N'-bis (3-aminopropyl)) or a combination thereof.

Figure 6:
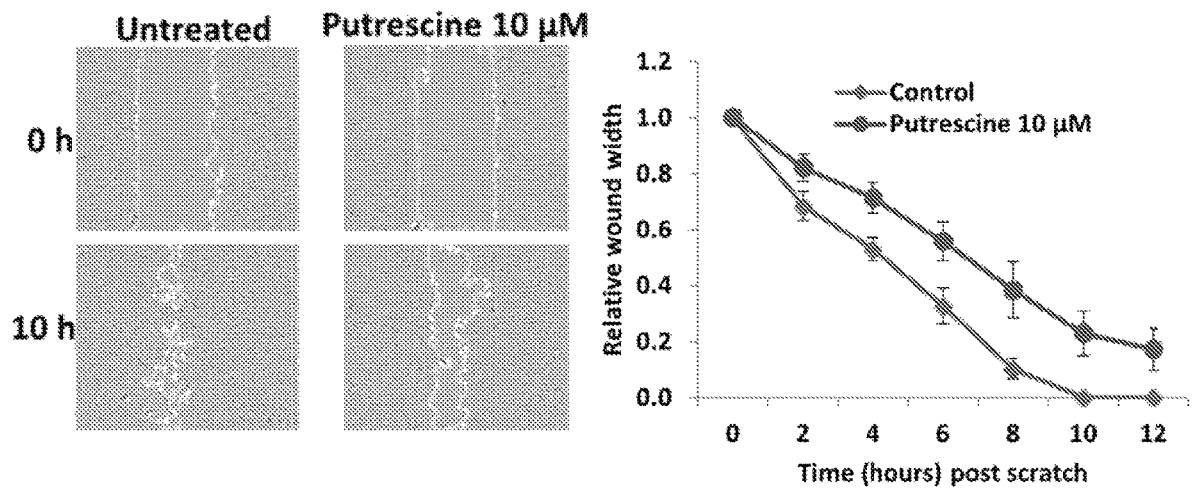
FIG. 6 shows data indicating that spermidine and spermine promote wound repair of excisional human skin wounds (a) Scratch assay showing addition of putrescine significantly impedes cell migration. (b) The effect of spermidine and spermine on migration of scratched keratinocytes. Spermine promotes the closure of scratch wounds in keratinocytes and restores impaired cell migration in sh-AMD1 keratinocytes. Images were taken at the indicated time points after scratch using the Incucyte Live Cell Analysis system. Cell migration was quantified by measuring the wound width at various time points after scratch and normalized to initial wound width made at time 0. Mean±standard error of three sets of independent experiments are shown. *$P \leq 0.05$. (c) H&E stained images of human skin before wounding and at 0 hours and 72 hours after wounding. Upon wounding, wounds were treated with 500 μM spermidine or spermine. Control wounds were treated with phosphate buffered saline (PBS). Treatment was administered daily for three consecutive days. New epithelial tongues extending from wound margin were indicated by the black-hatched lines. N=3. Scale bar=250 μm.
Figure 6:
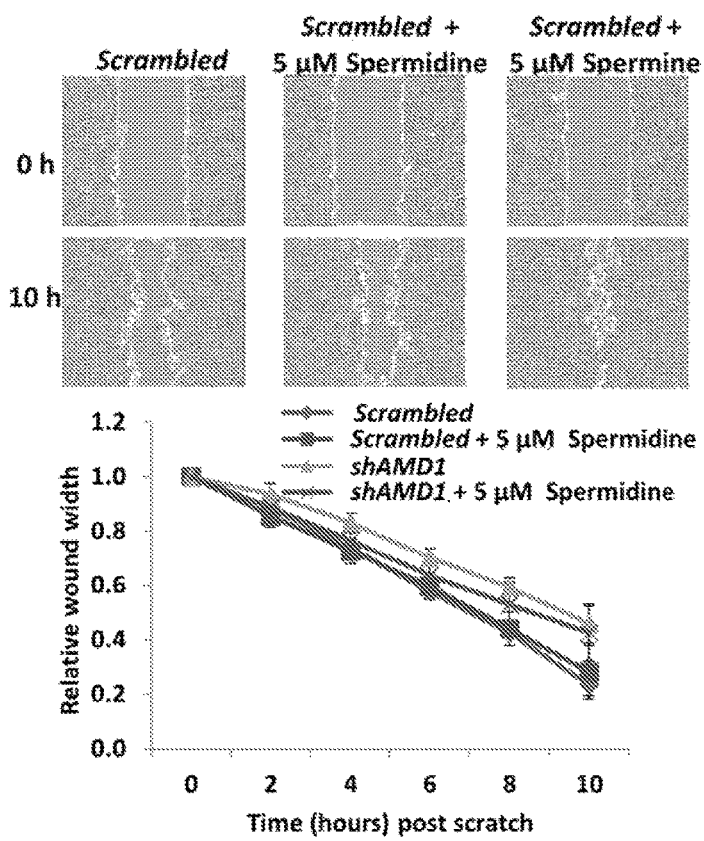
Figure 6:
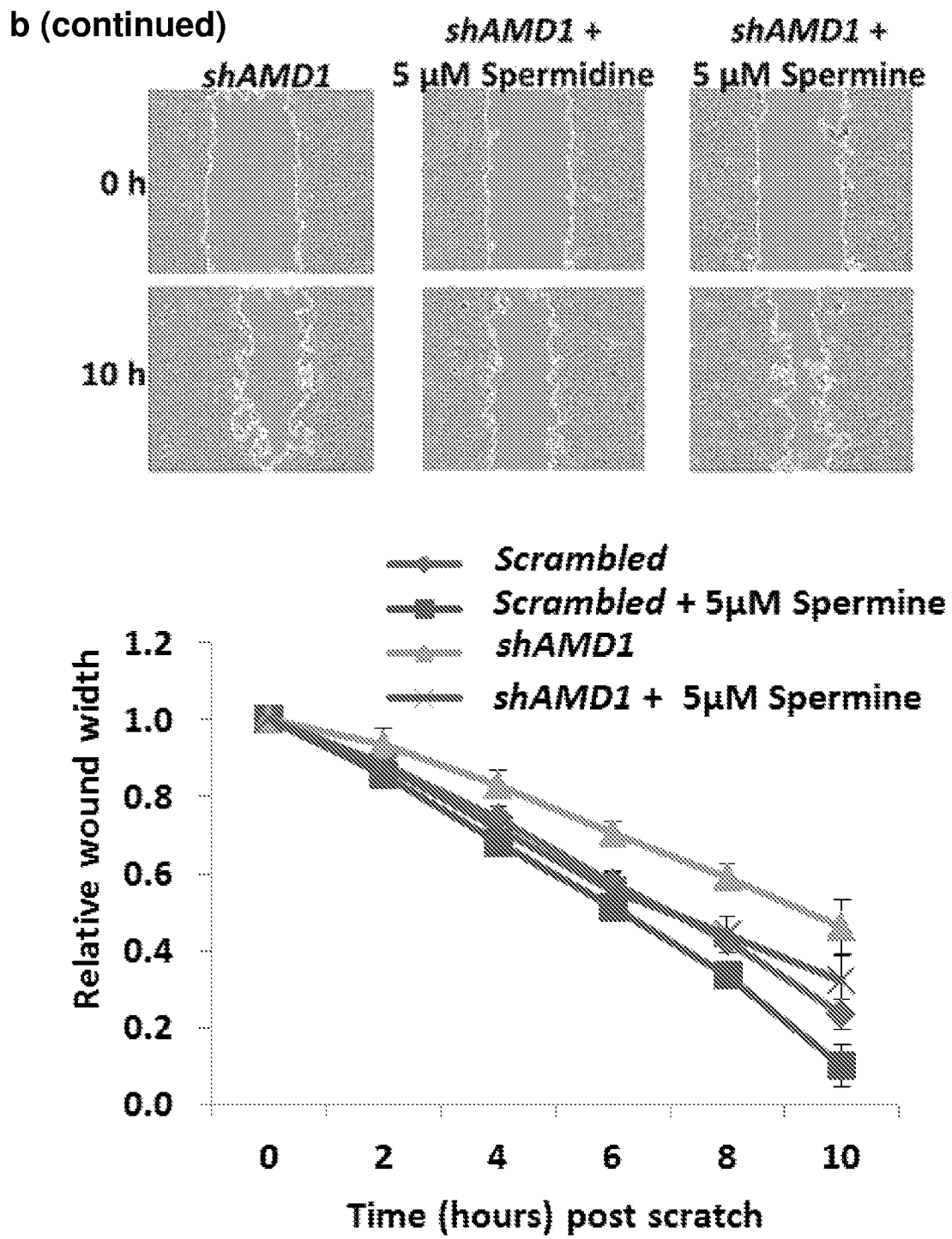
Figure 6:
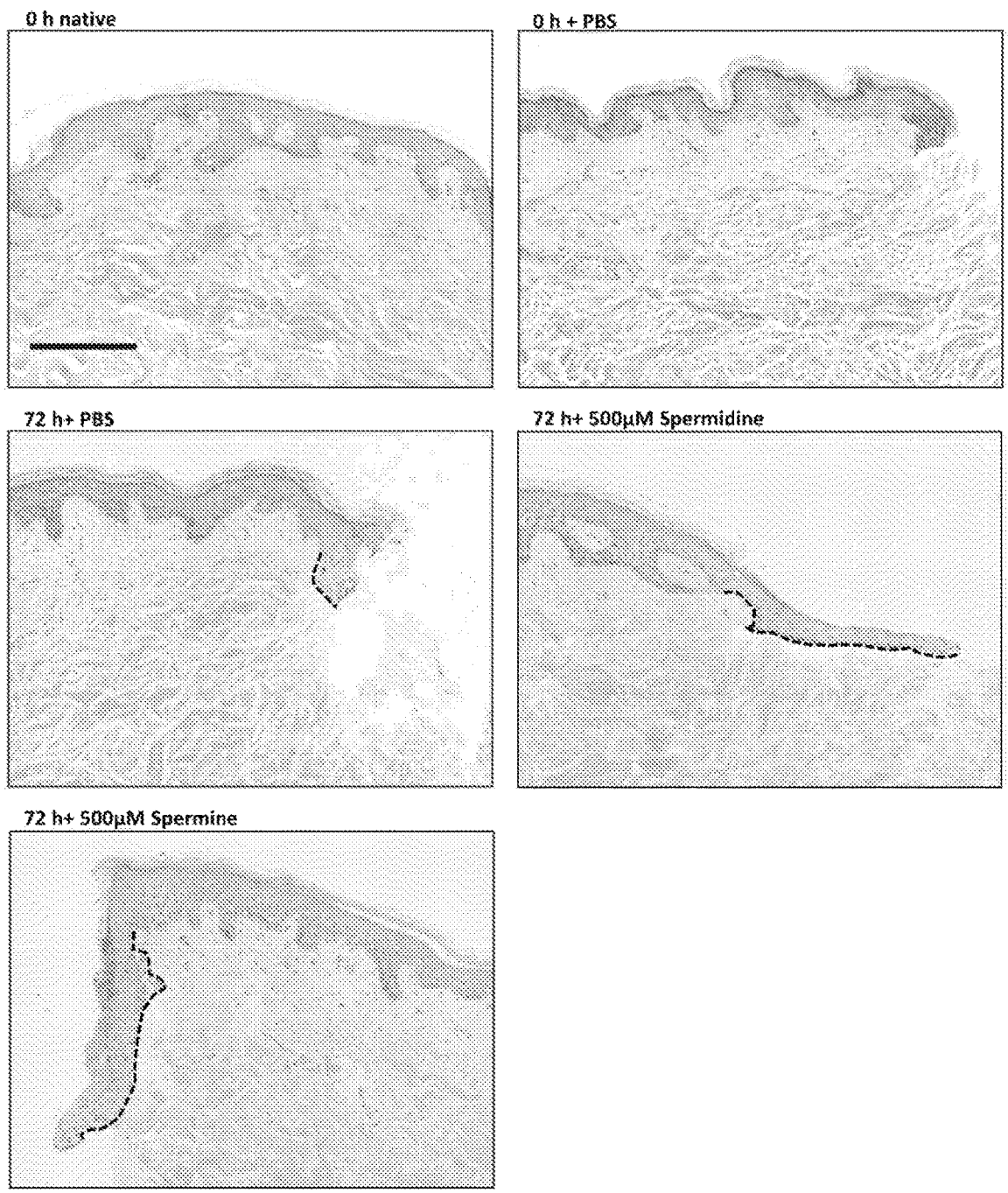

In one experiment, it was shown that when added to human ex vivo wounds and examining the length of the migrating tongue after 72 hours, spermine or spermidine promoted a striking improvement in epithelial tongue migration (FIG. 6c), thereby showing the role of spermine and spermidine played in enhancing cell migration.

In one example, the polycationic aliphatic amine is comprised in an amount of between 0.1 to 1 mM, between 0.25 to 0.5 mM, between 0.5 to 1 mM, between 0.75 to 0.9 mM, between 0.6 to 0.8 mM, about 0.4 mM, about 0.45 mM, about 0.5 mM, about 0.55 mM, about 0.6 mM, about 0.65 mM, about 0.8 mM or about 0.9 mM. In one example, the polycationic aliphatic amine is comprised in an amount of about 0.1 mM to 1 mM. In another example, the polycationic aliphatic amine is comprised in an amount of about 500 µM.

Polyamine catabolism also contributes to the regulation of polyamine levels, and increases in the SAT1 enzyme results in acetylation of spermine and spermidine. The acetylated polyamines are either converted back to spermidine or putrescine, respectively or are exported from the cell. Polyamine levels are tightly regulated in the cell and the rate-limiting regulators, AMD1 and ODC1, are regulated at the level of transcription, translation, protein stability, and activity to ensure the levels and ratios of the polyamines are appropriately maintained. While tightly controlled, the levels of the polyamines are altered in different cellular contexts to maintain normal cellular function. Controlled fluctuations of polyamine levels within physiological concentrations are seen in diverse tissues and cellular states such as in urine and blood during pregnancy, with age, and during cellular differentiation. Intracellular polyamine levels are up-regulated in response to injury and cellular damage to enable survival and regeneration of the injured tissues. While polyamines have been shown to play a role in repairing and healing of the gastric epithelium, very little is known about the role of polyamines in regulating barrier function or wound healing.

In normal skin, keratinocytes in the basal layer of the epidermis are in contact with the basement membrane and are proliferative. During differentiation, keratinocytes become detached, cease proliferating, and then stratify to form the skin barrier. On epidermal wounding, keratinocytes at the wound edge undergo a transition from a non-motile epithelial state to a mesenchymal-like state where they lose cell-cell contacts and become motile. Migrating cells reorganize their actin cytoskeleton and secrete proteases to remodel the extracellular matrix (ECM) and enable migration across the wound. Directly behind the migrating cells, keratinocytes rapidly proliferate to provide enough cells to cover the wound.

Keratinocyte migration is regulated by several factors, including growth factors and other components in the extracellular matrix. Many of these factors function through keratinocyte cell surface receptors to regulate intracellular signalling pathways that influence gene expression and cellular function. Defects in keratinocyte migration are characteristic of non-healing wounds, where re-epithelialization fails to occur.

Within seconds of wounding, there is a dramatic increase in intracellular calcium in the cells adjacent to the wound. This calcium flux moves as a wave from the wound edge, and is essential for wound healing to proceed. The increased calcium levels trigger changes in gene expression, in part through activation of PKC and CaMKs. This is essential for many aspects of wound healing, including reorganization of the actin cytoskeleton. Another non-transcriptional response to wounding is an increase in hydrogen peroxide ($H_2O_2$), which has a role in many different aspects of wound healing. Dangerous at high levels, it functions at low levels as a signalling molecule to promote wound closure and recruit immune cells to the wound site. In, for example, *Drosophila* fruit flies, calcium-dependent $H_2O_2$ gradients can be detected minutes after wounding. This increased $H_2O_2$ is generated by the NADPH oxidase DUOX. $H_2O_2$ is also produced at the leading edge of migrating cells in zebra fish and functions as a chemoattractant for immune cells. Intracellularly, increased $H_2O_2$ influences gene expression to promote cell.

The diamine, putrescine, and the higher order polyamines, spermidine and spermine, are naturally occurring cations present in all cells, and are essential for proliferation and a wide range of cellular events. Polyamine catabolism also contributes to the regulation of polyamine levels, and increases in spermidine/spermine N1-acetyltransferase 1 (SAT1) can result in acetylation of spermine and spermidine. The acetylated polyamines are either converted back to spermidine or putrescine, respectively, with the release of $H_2O_2$ or are exported from the cell. Polyamine levels are tightly regulated in the cell, whereas the rate-limiting regulators, AMD1 and ODC1, are regulated at the level of transcription, translation, protein stability, and activity to ensure the levels and ratios of the polyamines are appropriately maintained.

While tightly controlled, the levels of the polyamines are altered in different cellular contexts. Levels in urine and blood are increased during pregnancy and have been shown to decline with age. Indeed, spermidine has been suggested to also function as a longevity factor. Polyamine levels and ratios also change during cellular differentiation, as shown in neural differentiation of embryonic stem cells (ESCs), and have also been shown to influence muscle differentiation. High levels are present in proliferative cells, and many cancers show elevated levels of ODC1, which drives increased polyamine levels. While levels of polyamines are tightly controlled by enzymatic regulators to keep them within a physiologically appropriate range, controlled fluctuations within this range can promote different cellular phenotypes and have been indicated to play a regulatory role. Within the cell, it is estimated that spermine and spermidine predominantly exist in RNA-polyamine complexes, suggesting a role in RNA folding and function. In addition, polyamines modulate gene transcription and translation, kinase function, cytoskeleton assembly, and ion channel function.

Intracellular polyamine levels are up-regulated in response to injury and cellular damage, for example, during tissue regeneration in the brain following injury. This "polyamine response" is important for the survival and regeneration of the injured neurons. The polyamines are also modulated following, for example, ischemia reperfusion injury in the kidney, brain and heart, and play a role in the repair and healing of the gastric epithelium. Mucosal restitution requires migration of epithelial cells followed by cell proliferation to repair damaged tissue.

In rodents, inhibition of polyamines by addition of the ODC1 inhibitor, DFMO, prevents intestinal epithelial cell migration and proliferation, which can be rescued through supplementation with putrescine. The treatment of IEC-6 cells with DFMO and rescued with putrescine led to the identification of multiple gene regulatory events that depend on high polyamine levels, and are implicated in gastric epithelial repair.

Unlike the single-cell layer of the gastric epithelium, the epidermis of the skin consists of a stratified layer of keratinocytes and little is known about the role of polyamines in regulating barrier function or wound healing. In rat skin, ODC1 activity was shown to be increased during the early stages of wound healing, where its activity peaked at 12 hours and returned to normal by 48 hours. Ornithine supplementation has been suggested to improve wound healing in mice. Studies in rats showed that putrescine and spermidine were increased 12 hours after wounding, while spermine was only increased 4 to 7 days post wounding. Despite these observations, it remains unclear what drives these changes or how they impact the wound healing process.

Here, the role of the polyamine regulator, AMD1, in the wound healing process of the human epidermis is analysed. It was found that AMD1 is rapidly up-regulated in wound-edge keratinocytes, resulting in a shift in the ratios of polyamines such that the level of putrescine is decreased in favour of the levels of spermidine and spermine. Up-regulation of AMD1 is required for keratinocyte migration and plays a role in the activation of the uPAR/uPA signalling system. Failure to up-regulate AMD1 results in decreased uPA/uPAR protein levels and a failure of actin reorganization in the cells at the leading edge of the wound. It is further shown that AMD1 drives epithelial cell migration, in part, through the activity of SAT1, which promotes polyamine catabolism and increased levels of $H_2O_2$. The data indicates that, on wounding, polyamine levels are regulated within a physiological range and these changes function in a regulatory capacity during wound healing to promote cell behaviour changes that result in conversion of keratinocytes from a proliferative to a migratory phenotype to enable wound closure.

A shift in the relative levels of polyamines where the level of putrescine is decreased and the levels of spermidine and spermine are increased is required for efficient re-epithelialization during wound healing. Thus, when treating non-healing wounds, the attempt is made to mimic the normal healing environment, for example by manipulating the level of, for example, polyamines, in and around the area of the non-healing wound. This can be done by either increasing the level of specific effectors, or decreasing the level of other effectors.

Thus, in one example, the pharmaceutical composition is as disclosed herein, wherein the polycationic aliphatic amine is spermidine, spermine or a combination thereof. In another example, the function of ornithine decarboxylase 1 (ODC1) is inhibited. Thus, in a further example, the pharmaceutical composition disclosed herein comprises an ornithine decarboxylase 1 (ODC1) inhibitor. In yet another example, the inhibitor of ornithine decarboxylase 1 (ODC1) is, but is not limited to, siRNA, shRNA, (RS)-2,5-diamino-2-(difluoromethyl)pentanoic acid (α-difluoromethylornithine) (also known as DFMO; CAS no. 70052-12-9) and combinations thereof. In yet another example, the inhibitor of ornithine decarboxylase 1 (ODC1) is a shRNA. In another example, the inhibitor of ornithine decarboxylase 1 (ODC1) is a siRNA. In yet another example, the inhibitor of ornithine decarboxylase 1 (ODC1) is DFMO.

In one example, the pharmaceutical composition comprises any one of the following combinations: an ODC1 inhibitor combined with spermine; an ODC1 inhibitor combined with spermidine; decarboxylated S-adenosylmethionine combined with spermine; decarboxylated S-adenosylmethionine combined with spermidine; an ODC1 inhibitor combined with spermine and spermidine; decarboxylated S-adenosylmethionine combined with spermine and spermidine, and an ODC1 inhibitor combined with decarboxylated S-adenosylmethionine, spermidine and spermine.

Depending on the location of the wound to be treated, and if the subject is to be treated locally or systemically, the pharmaceutical compositions disclosed herein can be administered orally, intraadiposally, intraarterially, intraarticularly, intracranially, intradermally, intralesionally, intramuscularly, intranasally, intraocularally, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, orally, parenterally, rectally, subconjunctival, cutaneously, subcutaneously, sublingually, topically, transbuccally, transdermally, vaginally, in crèmes, in lipid compositions, via a catheter, via a lavage, via continuous infusion, via infusion, via inhalation, via injection, via local delivery, or via any combination thereof. In one example, the compositions disclosed herein are administered topically.

Also, depending on the location of the wound to be treated and the intended route of administration, the pharmaceutical composition disclosed herein can further comprise a pharmaceutically acceptable carrier and/or a pharmaceutically acceptable salt. In another example, the pharmaceutical composition can be provided as tablets, caplets, capsules, hard capsules, soft capsules, gelatine capsules, cachets, troches, lozenges, dispersions, suppositories, ointments, cataplasms, poultices, pastes, powders, dressings, creams, plasters, solutions, patches, wound dressings, aerosols, nasal sprays, inhalers, gels, suspensions, aqueous liquid suspensions, non-aqueous liquid suspensions, oil-in-water emulsions, a water-in-oil liquid emulsions, solutions, sterile solids, crystalline solids, amorphous solids, solids for reconstitution or combinations thereof. As a person skilled in the art will appreciate, which dosage form the pharmaceutical composition is provided as will depend on, for example, the route of administration, the location of the wound and the type of wound being treating.

In one example, the composition for topical administration comprises the composition as described herein and a dermatologically acceptable vehicle. The vehicle may be aqueous or non-aqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous non-aqueous or oil phase (oil-in-water emulsion), or a continuous non-aqueous or oil phase and a discontinuous aqueous phase (water-in-oil emulsion).

The pharmaceutical excipients used in the topical preparation of the present disclosure may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for a hydrophobic topical formulation include mineral oils, vegetable oils, and silicone oils. If desired, the composition as described herein may be dissolved or dispersed in a hydrophobic oil phase, and the oil phase may then be emulsified in an aqueous phase comprising water, alone or in combination with lower alcohols, glycerin, and/or glycols.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof, including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polydydric alcohol esters may be used as emulsifiers or emollients. Suitable polydydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

Lecithin and other phospholipids may be used to prepare liposomes containing the composition as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the composition as described herein to keratinocytes by fusing with the cell membrane of the keratinocytes.

In one example, the topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

Suitable viscosity enhancers or thickeners which may be used to prepare a viscous gel or cream with an aqueous base include sodium polyacrylate, xanthan gum, polyvinyl pyrolidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols.

Suitable preservatives and/or antioxidants for use in topical formulations include benzalkonium chloride, benzyl alcohol, phenol, urea, parabens, butylated hydroxytoluene (BHT), butylated hydroxyanisole (BHA), Tocopherol, and mixtures thereof.

Suitable chelating agents for use in topical formulations include ethylene diamine tetraacetic acid, alkali metal salts thereof, alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid.

The various examples of creams, ointments, lotions, solutions, gels, sprays and patches may incorporate the composition as described herein as the active ingredient, in combination with penetration enhancing agents and other active agents acting synergistically on the skin for the promotion of wound healing or wound closure or the treatment of non-healing wounds.

Disclosed herein are also methods of identifying and/or treating non-healing wounds, and/or slow healing wounds. Thus, in one example, there is disclosed a method of treating a wound in a subject, the method comprising administration of the pharmaceutical composition disclosed herein. In one example, the wound is characterised as being slow healing, or non-healing. In another example, the wound is considered to be acute. As used herein, the term "wound" refers to an injury to a body that typically involves laceration or breaking of a membrane, for example, such as the skin. Wounding may also include damage to underlying tissues, and is, in most cases, usually a result of an external, physical force on the body. A non-healing wound, for example, is a wound that does not heal according to an orderly set of stages and in a predictable amount of time the way most wounds do; wounds that do not heal within three months are often considered to be non-healing. Wounds can display a spectrum of healing rates, whereby acute and non-healing wounds lie at opposite ends of the spectrum. The term "wound" refers to all types of wound. As used herein, the term "subject" refers to an organism that is to be treated using the methods and compositions disclosed in the present application. It is understood that this category includes, for example, both human and non-human mammals. In relation to humans, the methods and compositions disclosed herein are to be use in the treatment of wounds present in such a subject, for example subjects with compromised wound healing capabilities. A possible reason for the occurrence of a wound can be, for example, due to pre-existing and/or underlying conditions or diseases, or because a subject is undergoing further treatment, whereby the further treatment results in impaired wound healing. These conditions or diseases may be pathological or non-pathological and can aggravate or exacerbate wound healing by being present in the subject. Examples of such conditions and/or diseases are, but are not limited to, cancer, diabetes (type I and type II), skin disorders, autoimmune disorders, inflammatory disorders (both internal and external) of the epithelial lining, the dermis and/or the sub-dermis, eczema, and the like. Thus, in one example, the subject is a subject suffering from, or thought to suffer from, an underlying condition or disease. IN another example, the subject is suffering from or thought to suffer from cancer. In another example, the subject is suffering from, or thought to suffer from, diabetes.

In another example, the subject is undergoing further treatment or has undergone further treatment, whereby the treatment is, but is not limited to, chemotherapy, chemoprevention, radiation therapy, immune suppressive therapy, steroid treatment, and the like. Thus, in one example, the subject is undergoing or has previously undergone chemotherapy. In one example, the method is as disclosed herein, wherein the subject suffers from an underlying condition or disease, or wherein the subject is undergoing further treatment.

Also disclosed herein are methods for promoting wound re-epithelialisation. As used herein, the term "re-epithelisation" refers to a process in which keratinocytes at the wound edge stop proliferating and start migrating to cover the wound.

Thus, in one example, there is disclosed a method of promoting re-epithelialisation of a wound, the method comprising at least one polycationic aliphatic amine to be administered to a subject in need thereof, wherein the polycationic aliphatic amine has at least 3 or more amino groups, of which two amino groups are terminal amino groups. In another example, the method further comprises administration of decarboxylated S-adenosylmethionine (also known as S-adenosylmethioninamine or AdometDC or dcAdoMet) or an inhibitor of ornithine decarboxylase 1 (ODC1), or both. In one example, the method further comprises administration decarboxylated S-adenosylmethionine (also known as S-adenosylmethioninamine or AdometDC or dcAdoMet) and an inhibitor of ornithine decarboxylase 1 (ODC1).

Also disclosed herein is a method of determining whether a subject is suffering from an acute or non-healing wound. In one example, the method comprises determining the level of at least one polycationic aliphatic amine in a sample obtained from the wound of a subject; comparing the levels of the at least one polycationic aliphatic amine with the levels of the same polycationic aliphatic amine found in a sample obtained from a subject without wound; wherein, upon comparison, an increased level of the at least one polycationic aliphatic amine in the wound sample is indicative of a non-healing environment; wherein the polycationic aliphatic amine(s) has at least 2 or more amino groups, of which 2 amino groups are terminal amino groups. In yet another example, the method further comprises determining the level of a second polycationic aliphatic amine in the same sample as previously obtained from the wound of a subject, wherein an increased level of the second polycationic aliphatic amine is indicative of a healing environment, and wherein decreased level of the second polycationic aliphatic amine is indicative of a non-healing environment. This is also shown in the experiments outlined in the present application, whereby immunofluorescence studies were performed using an antibody specific to spermidine and spermine, but not to putrescine. In non-scratched cells, the levels of spermine and spermidine were shown to be low. Within 6 hours of scratching, increased fluorescence was seen predominantly in wound-edge keratinocytes in a pattern similar to AMD1 (FIG. 4b), thus showing that the levels of spermidine and spermine are increased at the wound edge where cells are migrating.

In one example, the at least one polycationic aliphatic amine is but is not limited to, spermidine, spermine, putrescine and combinations thereof.

In one example, the sample is taken wound exudate, a wound edge or a wound centre. In another example, the sample contains cells taken from the wound edge or the wound centre.

As used herein, the term "wound progression" or "progression of wound healing" refers to the fact that, usually, wound healing occurs in an orderly manner, whereby the wound goes through defined set of stages and ultimately heals within a predictable amount of time. As it is possible to characterise each stage of healing that a wound progresses through, the present invention includes methods of determining at which stage of healing a wound is at the time of assessment. Thus, wounds that do not progress through the stages of wound healing or regress into previous stages, are likely to be, for example, non-healing. In one example, there is disclosed a method of determining progression of wound healing of a subject suffering from a wound, the method comprising determining the level of at least one polycationic aliphatic amine in a sample obtained from the wound of a subject; comparing the level of the at least one polycationic aliphatic amine with the level of the same polycationic aliphatic amine found in a sample obtained from a subject without wound; wherein, upon comparison, a decreased level of the at least one polycationic aliphatic amine in the wound sample is indicative of progression of wound healing, wherein an increased level of the at least one polycationic aliphatic amine in the wound sample is indicative of no progression or regression of wound healing; wherein the polycationic aliphatic amine(s) has at least 2 or more amino groups. In another example, the method further comprises determining the level of a second polycationic aliphatic amine in the same sample as previously obtained from the wound of a subject, wherein an increased level of the second polycationic aliphatic amine is indicative of progression of wound healing, and wherein decreased level of the second polycationic aliphatic amine is indicative of no progression or regression of wound healing.

In one example, the method does not have an effect on wound strength. That is to say that the methods disclosed herein do not have any effect on the strength of the wound. In another example, the methods disclosed herein result in an increase in keratinocyte migration, thereby resulting in more rapid wound closure. In yet another example, the methods disclosed herein do not involve fibroblasts.

In one example, the comparison of polycationic aliphatic amine levels in the methods disclosed herein is made between the wound of a subject and a sample obtained from a subject without wound.

In the event that the sample is indicative of a non-healing environment, the subject may then be administered pharmaceutical compositions disclosed herein.

In one example, the wound is cutaneous or subcutaneous.

In one example, the wound is an epithelial wound. In another example, the epithelial wound requires cell migration.

In one example, the wound is a surface wound. In a further example, the wound is an internal wound.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Polyamine Concentrations are Regulated During Cutaneous Wound Healing

AMD1 and ODC1 are the two major rate limiting enzymes in the polyamine biosynthetic pathway with AMD1 regulating the ratio of putrescine to spermidine and spermine. Immunofluorescence studies of AMD1 protein expression in wounded human skin biopsies showed that AMD1 was up-regulated as early as 6 h post injury in keratinocytes at the wound edge, and was maintained at 18 h post wounding (data not shown).

Immunofluorescence studies also demonstrated an increase in AMD1 expression at the wound edge of a scratched keratinocyte monolayer (data not shown). Rapid up-regulation of AMD1 was detected within 10 minutes of scratch wounding at the leading edge. By 1 hour post scratch, increased labelling of AMD1 could be detected over 18 cells deep from the wound edge. The up-regulated AMD1 was then redistributed to wound-edge keratinocytes two to five cells deep by 6 hours post scratch. It was shown that the rapid up-regulation of AMD1 is dependent on the calcium wave that moves back from the wound edge (data not shown). ODC1, a second rate-limiting enzyme in the polyamine synthesis pathway, was also mildly up-regulated in scratched keratinocytes (data not shown). While AMD1 shows a strong up-regulation in wound-edge cells, ODC1, a second rate-limiting enzyme, is only mildly up-regulated. This differential expression drives a shift in the levels and ratios of the polyamines promoting higher spermidine and spermine levels and decreased putrescine levels, which was confirmed by HPLC and IF analysis.

Intracellular polyamine levels were measured 6 and 12 hours post scratch and compared to non-scratched cells. The levels of putrescine were decreased by about 78% compared to non-scratched cells at 12 hours, consistent with an increase in AMD1 on wounding. There was no significant change in the levels of spermine or spermidine 6 hours or 12 hours post scratch likely due to the fact that only wound edge cells show increased levels and these are diluted out when all the cells are harvested (data not shown). Immunofluorescence studies using an antibody specific to spermidine and spermine but not to putrescine showed that within minutes following scratch there were substantially increased levels of spermidine and spermine in the wound edge keratinocytes and this persisted at 6 hours (data not shown). This was confirmed in human ex vivo skin wounds, where wound-edge keratinocytes showed increased spermine and spermidine staining at 6 hours and 18 hours post wounding compared with 0 hour wounded sections (data not shown).

AMD1 is Up-Regulated During Keratinocyte Differentiation

Polyamine levels are known to be elevated in the epidermis compared with the dermis, but their function is not well understood. Polyamine regulator AMD1 is rate limiting for the conversion of putrescine to spermidine and spermine, therefore changes in its activity influence the putrescine to spermine/spermidine ratio. To address the role of AMD1 in the human epidermis, AMD1 expression in human skin histological sections was analysed by immunofluorescence. AMD1 was highly expressed in the more differentiated granular layer of the epidermis and was present at low levels in the proliferating basal cell layer (FIG. 1a). AMD1 protein levels were also up-regulated in the N/TERT-1 human keratinocyte cell line following six days of calcium-induced differentiation, first detectable by day two and peaking at day four (FIG. 1b). The terminal differentiation markers, involucrin (IVL) and filaggrin (FLG), were also up-regulated, confirming the efficiency of cell differentiation (FIG. 1b).

AMD1 is Transiently Up-Regulated During Cutaneous Wound Healing

To determine if AMD1 protein is up-regulated on wounding, immunofluorescence studies of AMD1 expression were performed on wounded human skin biopsies. AMD1 expression was shown to be up-regulated as early as 6 hours post injury in keratinocytes at the wound edge, and was maintained at 18 hour post wounding (FIG. 1c). Immunofluorescence studies also indicated an increase in AMD1 expression at the wound edge of a scratched keratinocyte monolayer (FIG. 1d). Rapid up-regulation of AMD1 was detected within 10 minutes of scratch wounding at the leading edge. By 1 hour post scratch, increased labelling of AMD1 could be detected over 18 cells deep from the wound edge. The up-regulated AMD1 was then redistributed to wound-edge keratinocytes two to five cells deep by 6 hours post scratch. AMD1 up-regulation on wounding was confirmed by western blot and qRT-PCR on scratched keratinocyte cultures (FIG. 1e,f). mRNA expression of ODC1, a second rate-limiting enzyme in the polyamine synthesis pathway, was also up-regulated in scratched keratinocytes (FIG. 1f). However, while the up-regulation of ODC1 and AMD1 at the RNA level look similar, the distribution and level of up-regulation in wound-edge keratinocytes is very different as seen by immunofluorescence (FIG. 1g). AMD1 shows a strong up-regulation in wound-edge cells while ODC1 protein is only mildly up-regulated many cells back from the wound edge. No change was observed in the levels of spermine synthase (SMS1), which is not believed to be rate limiting (FIG. 1e,f).

Upregulation of AMD1 is Stimulated by Scratch-Induced Calcium Waves

Figure 2:
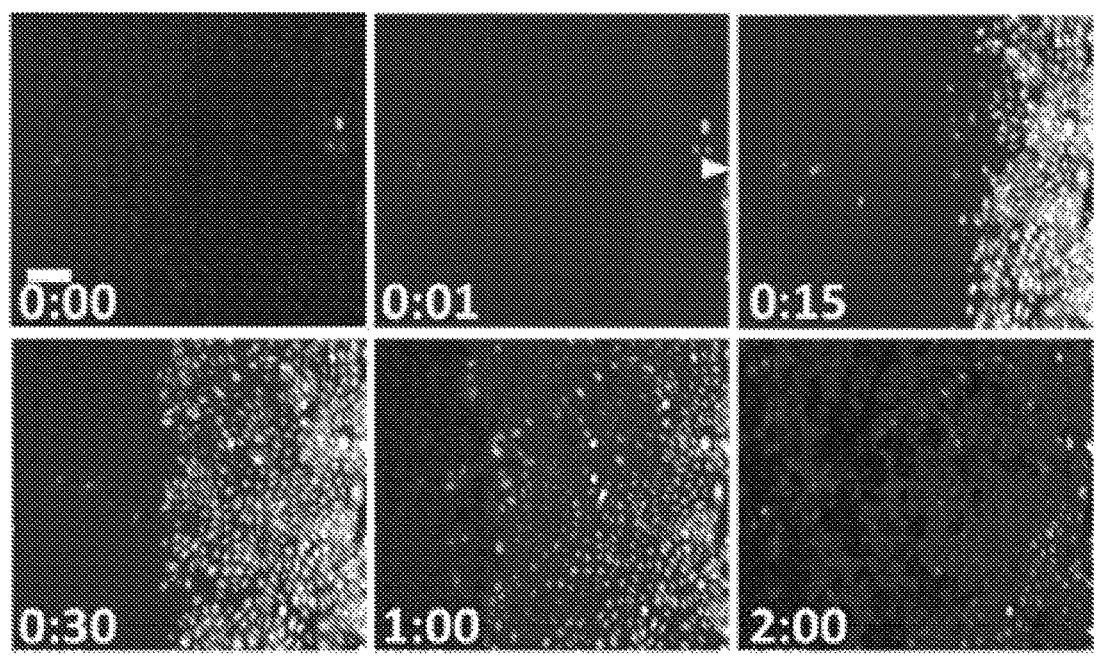
FIG. 2 shows results of experiments indicating that AMD1 upregulation is stimulated by scratch-induced calcium waves. (a) $Ca^{2+}$ probe Fluo-4 labelling (1 μg/mL) revealed a calcium wave spreading outward upon scratch from the scratch-wound margin. The time labels (seconds) reflect the time points post scratch. White arrow heads indicate site of scratch wound. (b) Kinetics of calcium wave propagation after scratch from images taken in (a). (c) Pre-treatment of keratinocytes with 1 μM Tg (24 hours) and 2 mM EGTA (1 hour) abrogates the propagation of calcium wave upon scratch. Scale bar=50 μm. (d,e) Scratches were made in confluent keratinocytes with and without Tg and EGTA pre-treatment. Immunofluorescence staining and western blot demonstrating impeded AMD1 upregulation post scratch following Tg and EGTA treatment. Scale bar=100 μm. NS denotes no scratch.
Figure 2:
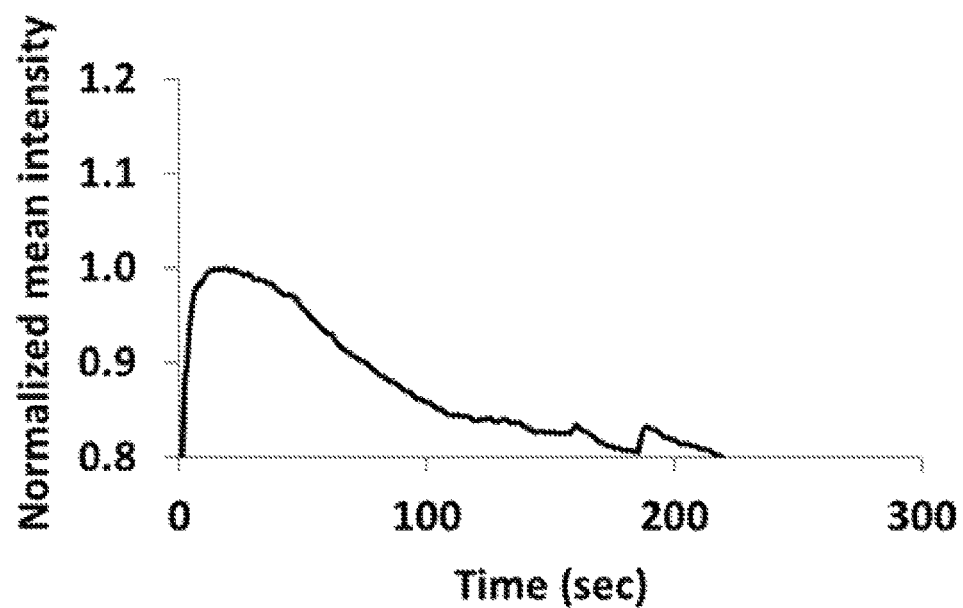
Figure 2:
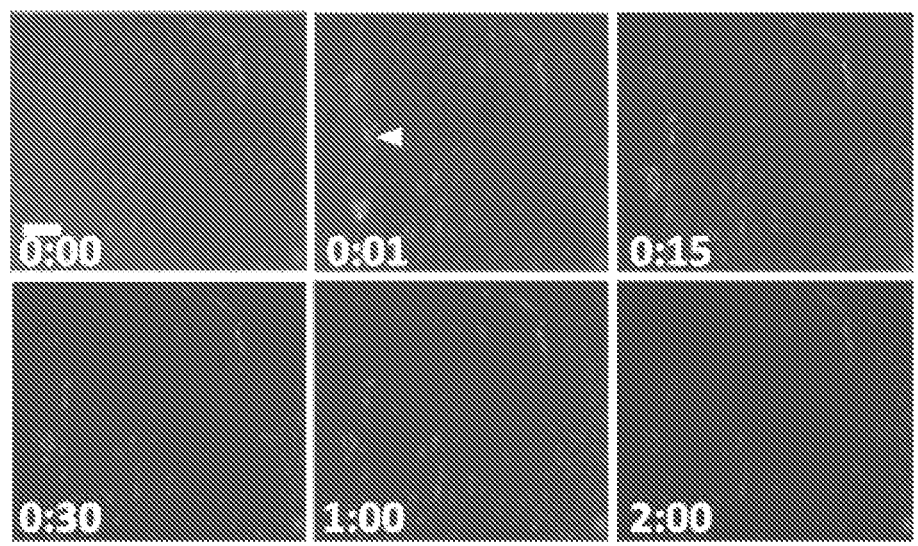
Figure 2:
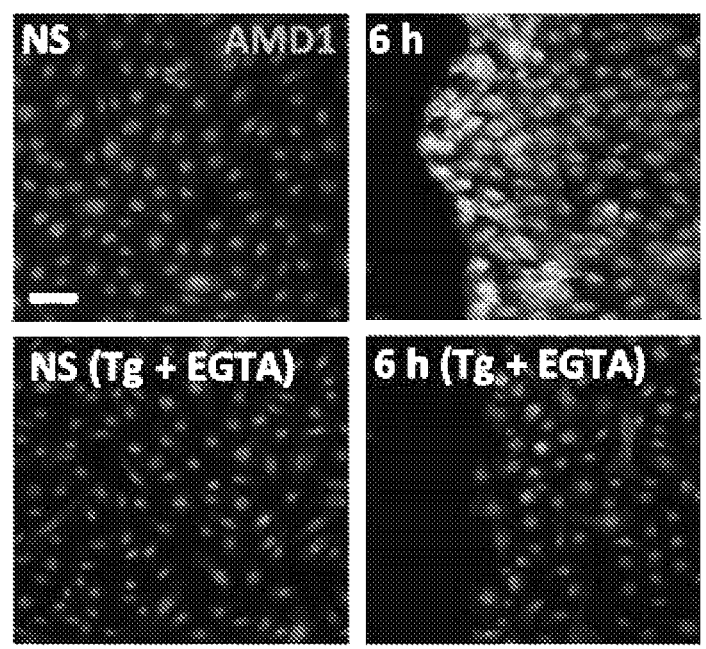
Figure 2:
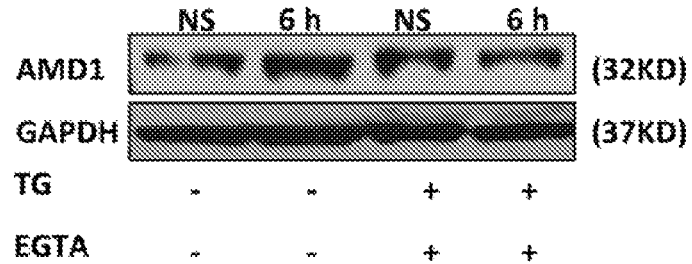

It was then sought to determine if the up-regulation of AMD1 at the wound-edge was dependent on the wound-induced calcium wave. Human keratinocytes were labelled with the $Ca^{2+}$ probe Fluo-4 for 30 minutes prior to scratching to mimic a wound response. Live-cell imaging of the scratch wound edge demonstrated a rapid calcium flash extending outward from the point of scratch as a wave (FIG. 2a). Quantitative analysis of the calcium flash kinetics showed that the calcium signal peaked at 17 seconds post scratch. After this initial rapid elevation of intracellular calcium, the signal subsequently decayed to background level after 3 minutes (FIG. 2b). To assess the impact of a reduced calcium wave on up-regulation of AMD1, cells were pre-treated for 24 hours with 1 µM thapsigargin (Tg) and for 1 hour with 2 mM EGTA prior to scratch to deplete internal calcium stores and extracellular calcium, respectively. Live imaging with the Fluo-4 probe revealed that addition of the drugs effectively prevented the calcium wave following the scratch (FIG. 2c). AMD1 up-regulation in the scratched cells was completely abrogated following calcium-blocking, as shown by immunofluorescence and western blot of cells 6 hours post scratch (FIGS. 2d and 2e). This suggests that the calcium wave is required for AMD1 up-regulation in the wound edge keratinocytes. Collectively, this data indicates that AMD1 up-regulation on wounding is downstream of the calcium wave.

AMD1 Up-Regulation is Required for Cell Migration on Wounding

The polyamine shift seen on wounding is dependent on AMD1, as shown by knocking down the relevant mRNA using short hairpin RNAs (shRNAs). Knockdown of AMD1 results in a failure to shift polyamine levels on wounding, as demonstrated by HPLC analysis and IF using the spermine/spermidine antibody. (data not shown). To determine the function of AMD1 up-regulation in keratinocytes during wound healing, in vitro wound healing assays were performed on AMD1-knockdown human keratinocytes.

Figure 3:
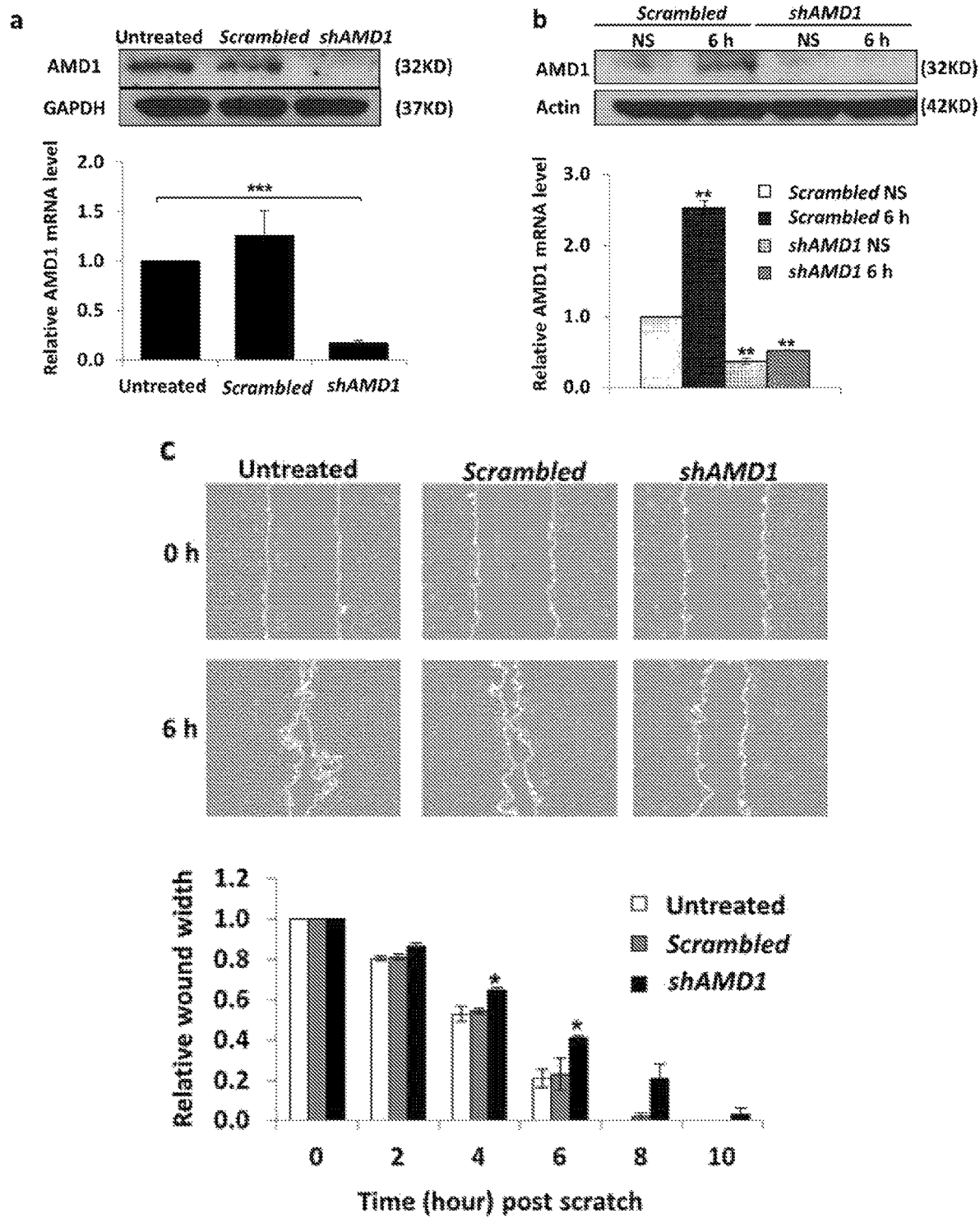
FIG. 3 shows data showing that AMD1 up-regulation is required for cell migration on wounding. (a) Western blot and RT-PCR results showing AMD1 levels in keratinocytes expressing scrambled and AMD1 shRNA. (b) Western blot and RT-PCR results showing increase in AMD1 expression 6 hours post scratch in sh-scrambled cells compared with shAMD1 cells. (c) Cell migration of sh-scrambled and shAMD1 keratinocytes were monitored by in vitro scratch assay. Light micrograph of wounded cell monolayer showing impaired wound closure at 6 hours in shAMD1 keratinocytes using the Incucyte Live Cell Analysis system. Relative wound width was quantified using Incucyte software by measuring wound width at various time points after scratch. Data was normalized to initial wound width made at time 0. (d) uPAR and uPA protein upregulation in scratched human keratinocytes measured by western blot. GAPDH is shown as a loading control (e) Western blot showing up-regulation of uPAR and uPA in sh-scrambled and sh-AMD1 scratched keratinocyte monolayers. Quantification of band intensities is plotted in the column graph below. N=3. (f) Immunostaining of uPA in sh-scrambled and sh-AMD1 scratched keratinocyte monolayers. Scale bar=50 (g) Fluorescence imaging of human wound sections stained with uPAR (red, n=3), showing increased expression at the wound edge at 24 hours post wounding. Hoechst DNA stain is shown. Scale bar=50 μm. (h) Immunostaining of F-actin with Hoechst DNA stain showing increased expression of F-actin at the wound edge of sh-scrambled control cells compared to sh-AMD1 knockdown cells. Scale bar=25 μm. NS denotes no scratch. Mean±standard error of three sets of independent experiments are shown. *$P \leq 0.05$, $P \leq 0.01$ and *$P \leq 0.001$.
Figure 3:
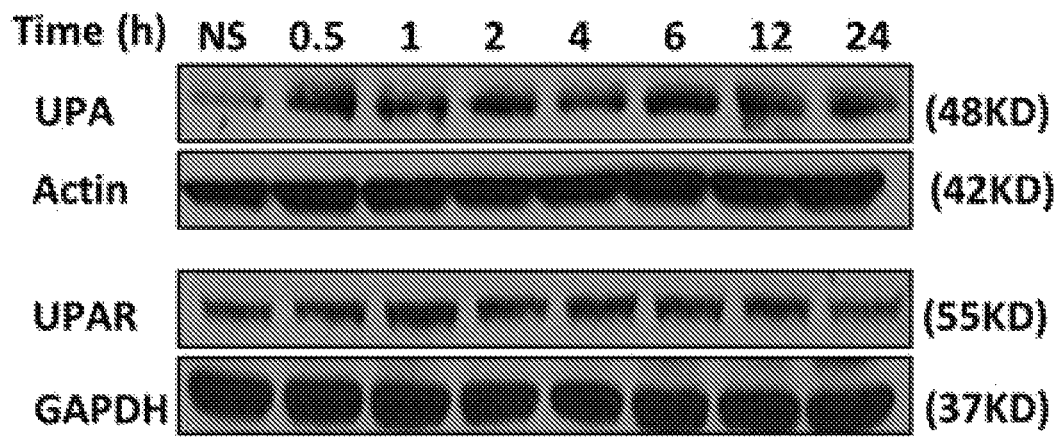
Figure 3:
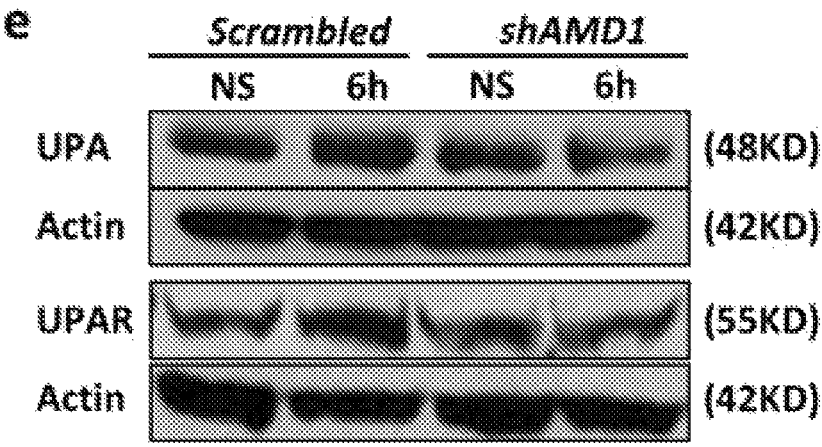
Figure 3:
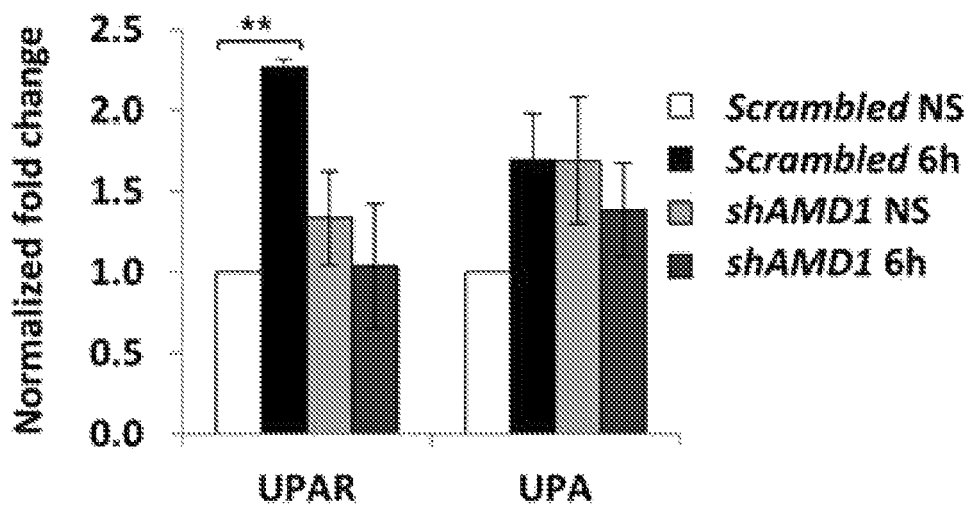
Figure 3:
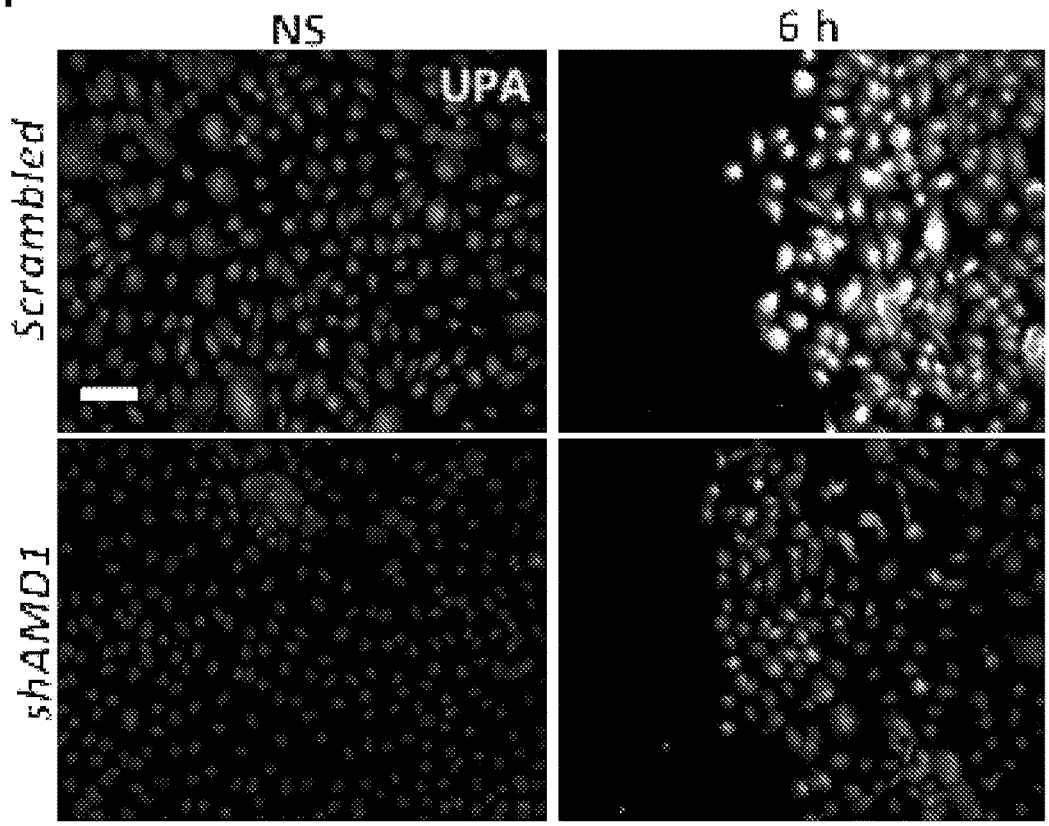
Figure 3:
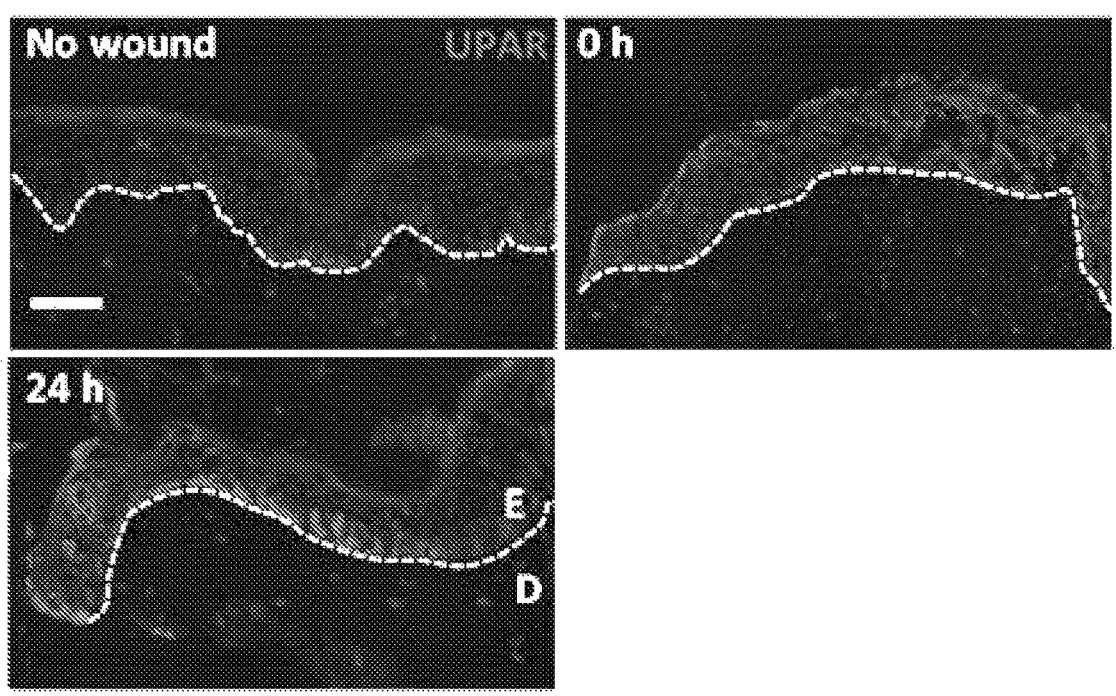
Figure 3:
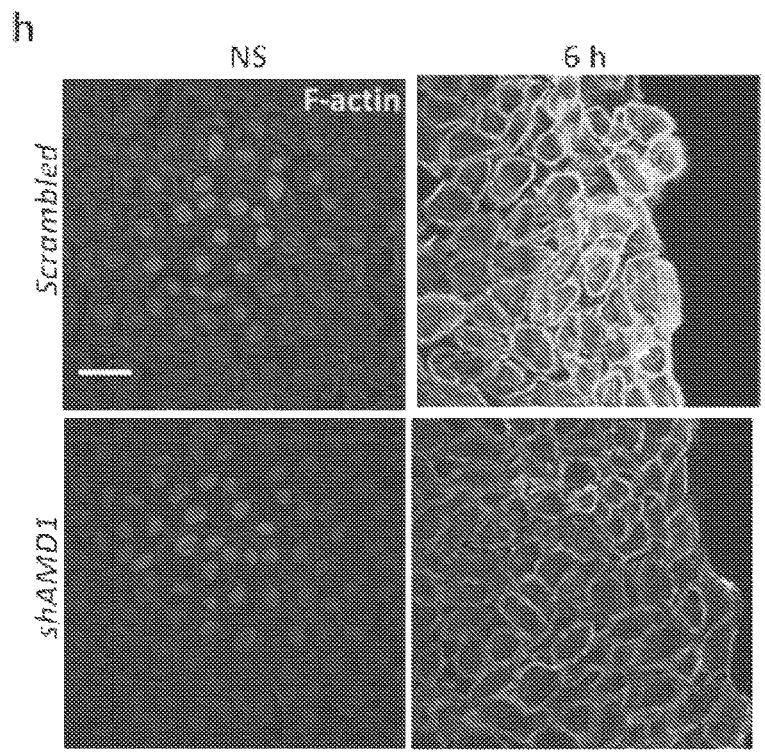

Keratinocytes expressing shRNAs targeting AMD1 showed a 70-80% decrease in AMD1 RNA and protein expression (FIG. 3a). shRNA-expressing cells failed to up-regulate AMD1 RNA or protein expression on wounding compared with scrambled control cells (FIG. 3b). The absence of AMD1 up-regulation resulted in a significantly delayed wound closure in a scratch assay (FIG. 3c). At 6 hours post scratch, AMD1 knockdown resulted in a 20% increased relative wound width compared with control cells.

In summary, shAmd1-expressing keratinocytes failed to up-regulate AMD1 protein on wounding compared with scrambled control cells (data not shown). The absence of AMD1 up-regulation resulted in a significantly delayed wound closure in a scratch assay (data not shown). It was further shown that the inhibition of cell migration and wound closure, induced by a knockdown of AMD1, could be rescued by the addition of spermine to the cell culture media. This confirms the role of AMD1 and spermine/spermidine in wound edge keratinocytes in promoting cell migration.

Addition of an inhibitor to AMD1, EGBG, resulted in a similar delay in cell migration and was similarly rescued by the addition of spermine (data not shown).

Figure 8:
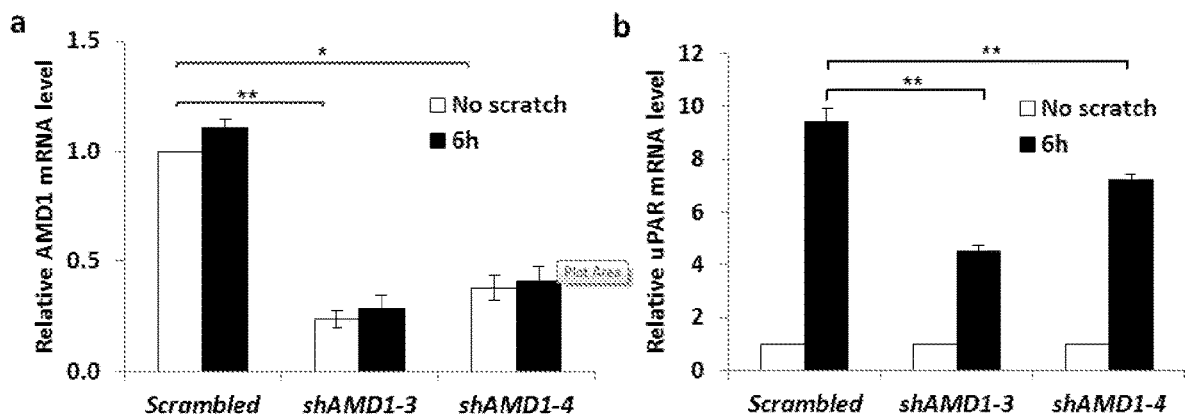
FIG. 8 shows data illustrating that AMD1 up-regulation is required for cell migration on wounding. (a) RT-PCR showing AMD1 levels in keratinocytes expressing scrambled and sh3 and sh4 AMD1 RNA. (b) RT-PCR showing relative uPAR mRNA levels in keratinocytes expressing scrambled and sh3 and sh4 AMD1 RNA. (c) In vitro scratch assay showing cell migration of sh-scrambled and sh3 and sh4 AMD1 keratinocytes monitored by light microscopy of wounded cell monolayers. Sh3 and sh4 AMD1 keratinocytes show impaired cell migration using the Incucyte Live Cell Analysis system. Relative wound width was quantified using Incucyte software by measuring wound width at different time points after scratch. Data normalized to 0 hour wound width. (d) Immunostaining of uPA in sh-scrambled and sh3 and sh4-AMD1 keratinocyte monolayers before and 6 hours after scratch.
Figure 8:
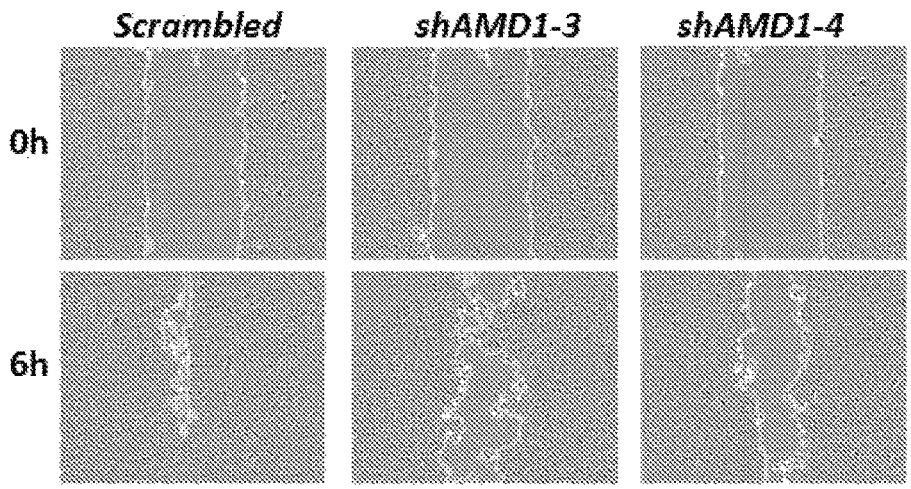
Figure 8:
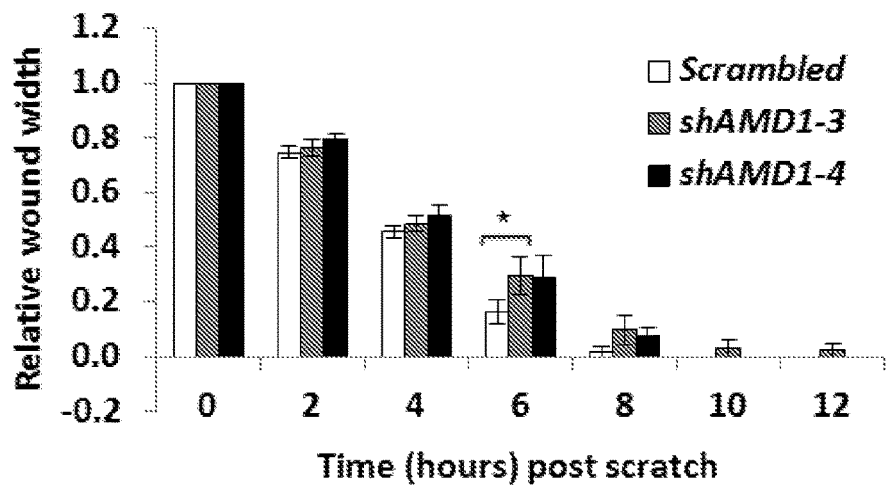
Figure 8:
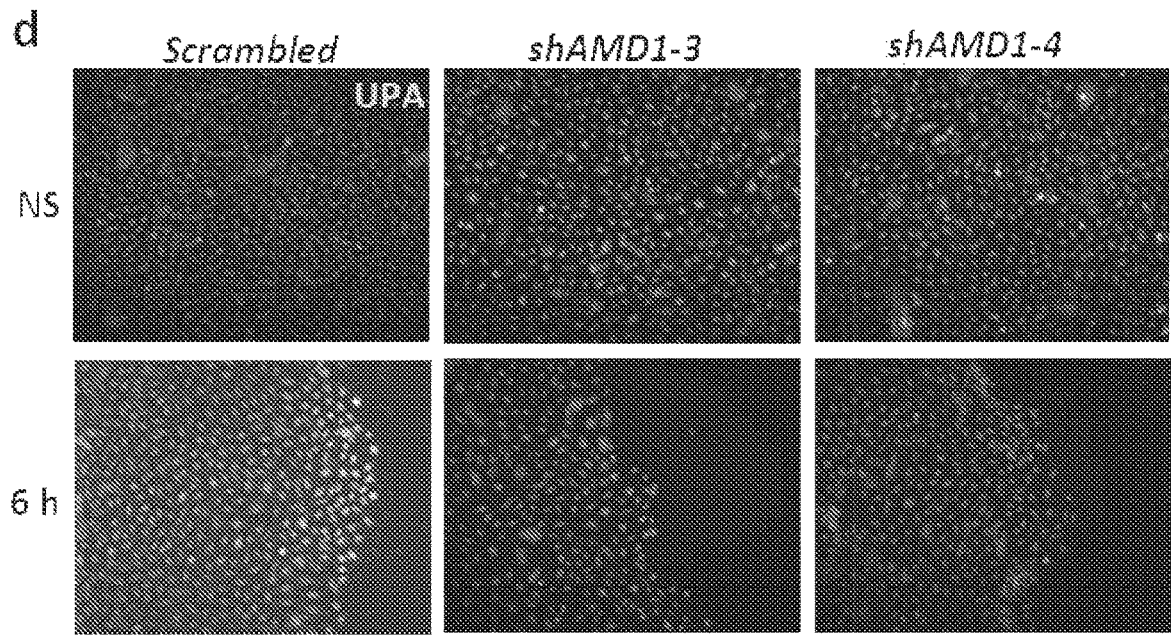
Figure 9:
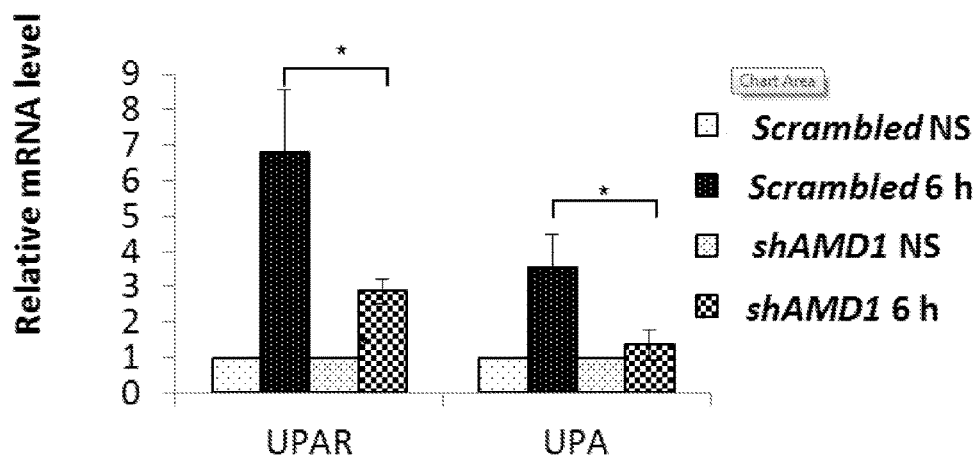
FIG. 9 shows RT-PCR data showing relative uPAR and uPA mRNA levels in keratinocytes before and after scratch in scrambled and sh3 AMD1.
Figure 10:
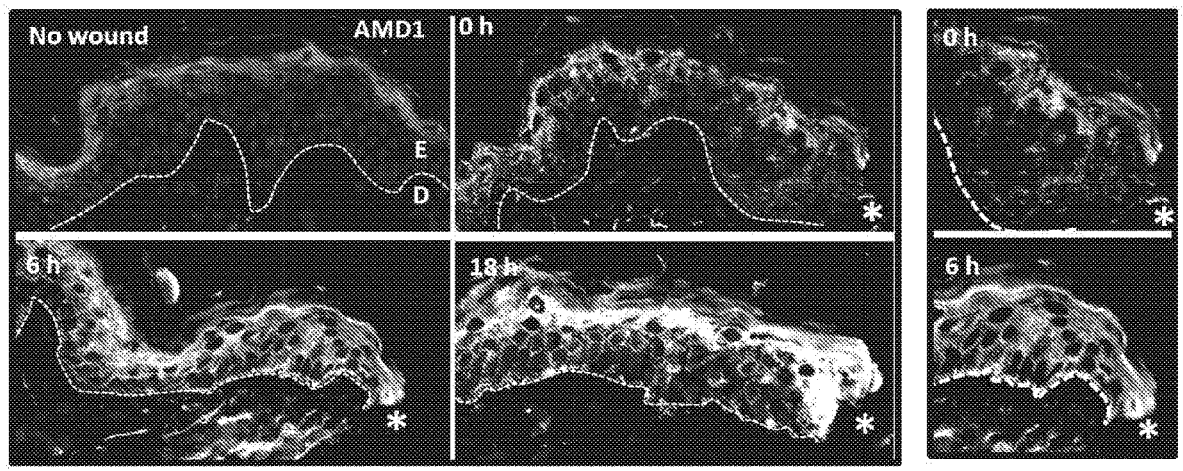
FIG. 10 shows data illustrating that AMD1 is upregulated in wound-edge keratinocytes. Immunofluorescence of AMD1 expression in skin biopsies from healthy donors before and 0, 6 and 18 hours wounding (n=3) counterstained with Hoechst (DNA). Scale bar=25 μm. E denotes epidermis; D denotes dermis. AMD1 is expressed in the more differentiated layers of the skin epidermis and is upregulated in wound edge keratinocytes. Right panels show enlarged wound edge cells showing AMD1 staining at 0 and 6 hours.
Figure 11:
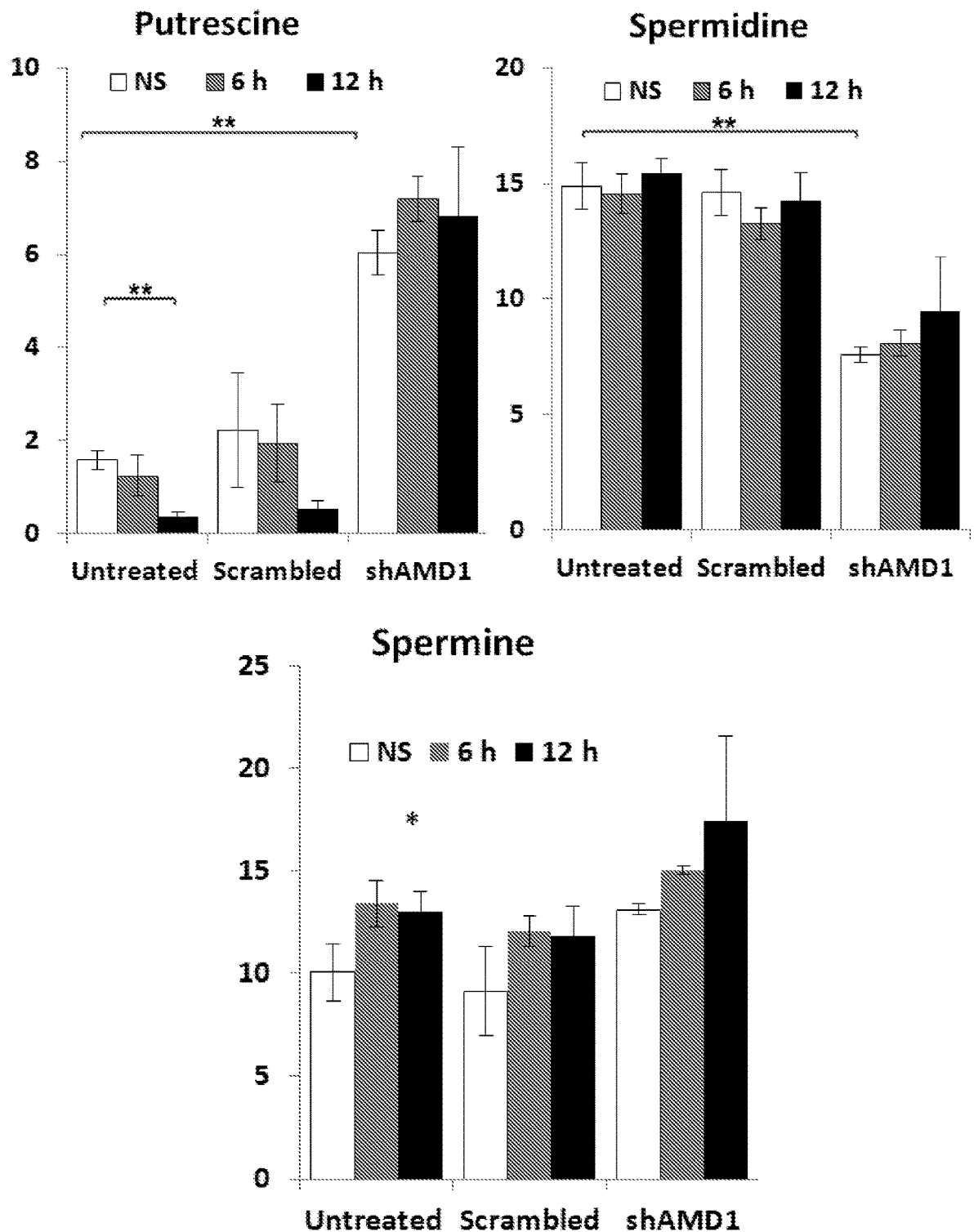
FIG. 11 shows column graphs showing data illustrating that wounding causes a shift in polyamine ratios at the wound edge. HPLC analysis showing changes in polyamine levels in N/TERT-1 control, sh-scrambled and shAMD1 keratinocytes before and after scratch (6 and 12 hours). Mean±standard error of three sets of independent experiments are shown. $*P \leq 0.05$ and $**P \leq 0.01$.
Figure 12:
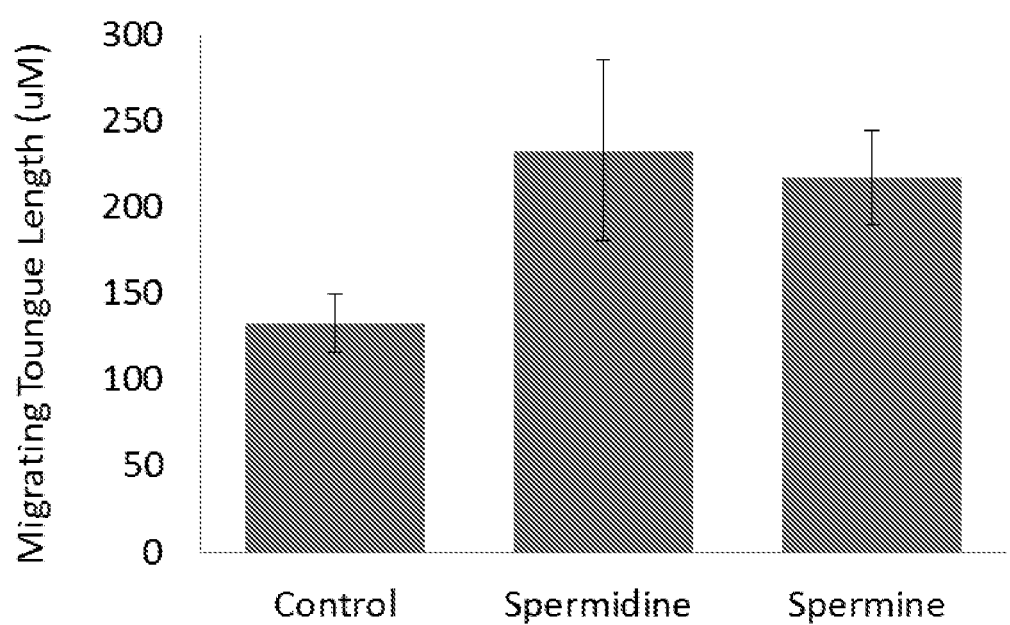
FIG. 12 shows a column graph showing that spermidine and spermine promote wound repair of excisional human skin wounds. The quantification of the data shown in the micrograph images of FIG. 6c is shown as column graphs. Epithelial tongue length was quantified following spermine or spermidine treatment (n=6). Mean±standard error of three sets of independent experiments are shown. $*P \leq 0.05$.

To determine the mechanism by which AMD1 promotes cell migration, the effect of knockdown on expression of proteins known to be required for cell migration was determined. The urokinase plasminogen activator receptor (uPAR) and urokinase plasminogen activator (uPA) are up-regulated on wounding and function to promote reorganization of the actin cytoskeleton at the leading edge of migrating cells and to degrade the extracellular matrix (ECM), allowing the migrating cells to move freely. Western blot analysis of keratinocytes at 0 hours and 6 hours post scratch indicated that uPA and uPAR proteins are rapidly up-regulated on wounding with similar kinetics to AMD1 (FIG. 3d, FIG. 8). There was also a marked up-regulation of uPAR and uPA mRNA levels (9.8-fold and 3.6-fold, respectively) in scratched control cells (FIG. 9). Strikingly, uPA and uPAR up-regulation post scratch is impeded when AMD1 is knocked down (FIG. 3e). Western blot analyses on scratched cells are subject to a significant dilution effect as only the cells at the wound edge are migrating. To confirm the AMD1-dependent up-regulation of uPA in wounded keratinocytes, immunofluorescence staining of uPA was performed in scratched keratinocytes. uPA expression was shown to be up-regulated at the wound edge in control cells, but not in AMD1-knockdown cells post wounding (FIG. 3f). Analysis of ex-vivo human skin histological sections indicated that up-regulation of uPAR is present at 24 hours post wounding (FIG. 3g). Activation of uPAR by uPA binding results in reorganization of the actin cytoskeleton to promote cell migration. To assess the effect of AMD1 depletion on F-actin reorganization upon wounding, cytoskeletal F-actin was visualized using fluorescein-labelled phalloidin in control and AMD1-knockdown cells (FIG. 3h). In scratched control cells, an increase in F-actin was seen in cells located at the wound edge. Cells exhibiting an up-regulation of AMD1 also showed an increase in actin filaments. In shAMD1-knockdown cells, actin failed to reorganize at the wound edge 6 hours post scratch. These results indicate that AMD1 promotes cell migration during wound healing by up-regulating uPA/uPAR, which in turn drives actin filament reorganization to enable cell migration.

For re-epithelialization to occur keratinocytes at the wound edge undergo an epithelial to mesenchymal like shift that enables migration. The urokinase plasminogen activator receptor (uPAR) and urokinase plasminogen activator (uPA) are up-regulated on wounding and function to promote reorganization of the actin cytoskeleton at the leading edge of migrating cells and to degrade the ECM, allowing the migrating cells to move freely. Immunofluorescence analysis of keratinocytes at 0 hours and 6 hours post scratch indicated that uPA and uPAR proteins are rapidly up-regulated on wounding with similar kinetics to AMD1 (data not shown). This up-regulation is impeded when AMD1 is knocked down (data not shown). Activation of uPAR by uPA binding results in reorganization of the actin cytoskeleton to promote cell migration. To assess the effect of AMD1 depletion on F-actin reorganization upon wounding, cytoskeletal F-actin was visualized using fluorescein-labelled phalloidin in control and AMD1-knockdown cells (data not shown). In scratched control cells, an increase in F-actin was seen in cells located at the wound edge. Cells exhibiting an up-regulation of AMD1 also showed an increase in actin filaments. In shAMD1-knockdown cells, actin failed to reorganize at the wound edge 6 hours post scratch. These results suggest that AMD1 promotes cell migration during wound healing by up-regulating uPA/uPAR, which in turn drives actin filament reorganization to enable cell migration.

Keratinocyte Polyamine Levels Shift after Wounding

Figure 4:
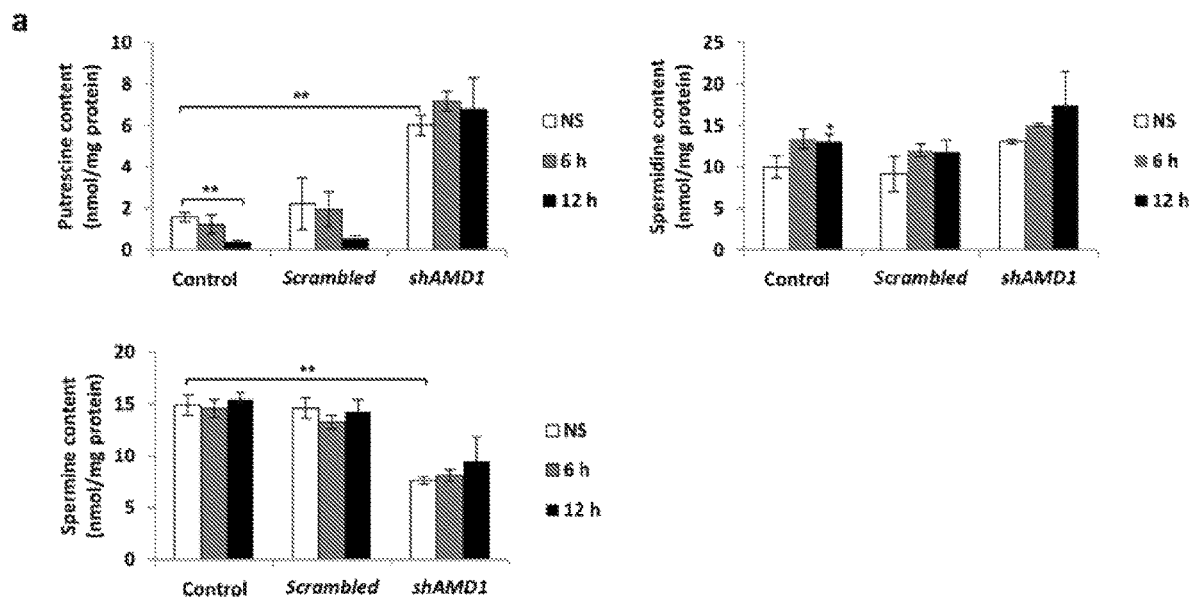
FIG. 4 shows column graphs and micrograph images of stained samples, illustrating that wounding causes a shift in polyamine ratios at the wound edge. (a) HPLC analysis showing changes in polyamine levels in N/TERT-1 control, sh-scrambled and shAMD1 keratinocytes before and after scratch (6 and 12 hours). (b,c) Immunostaining of spermine and spermidine (Spm and Spd) with Hoechst DNA stain showing time-dependent upregulation of spermine and spermidine at the wound edge in scratched monolayer keratinocytes (b) and human ex vivo wounds (c). Scale bar=25 μm (b), 50 (c). Mean±standard error of three sets of independent experiments are shown. NS denotes no scratch. *$P \leq 0.05$ and **$P \leq 0.01$.
Figure 4:
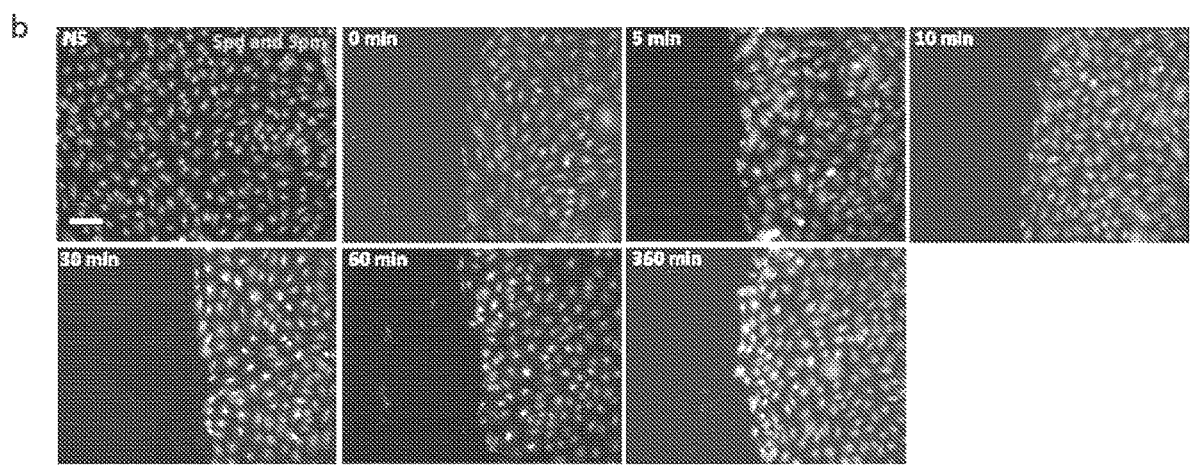
Figure 4:
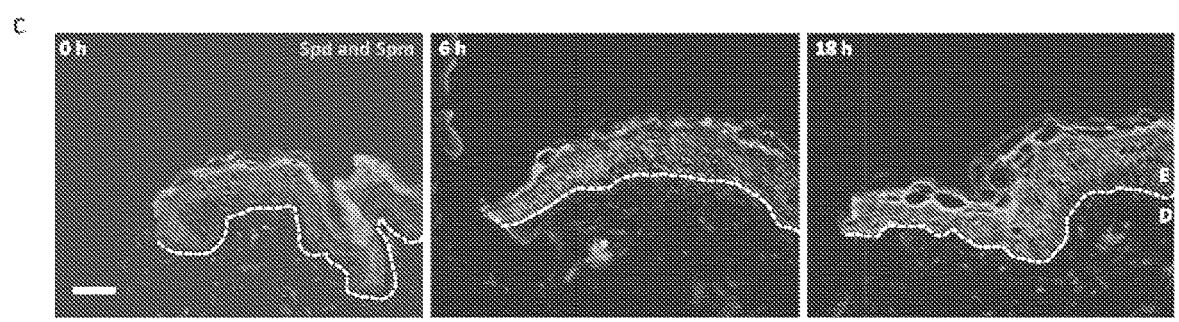

The data shows that AMD1 is up-regulated in keratinocytes at the wound edge post injury. Changes in AMD1 alter the availability of the aminopropyl donor dcAdoMet required for the generation of spermidine and spermine. As a consequence, increases in AMD1 were thought to alter the ratio of putrescine to spermidine and spermine. To investigate this further, intracellular polyamine levels were assessed in control keratinocytes and AMD1-knockdown keratinocytes 6 hours and 12 hours post scratch assay. As expected, in normal keratinocytes, the levels of putrescine were decreased by about 78% compared to non-scratched cells at 12 hours, consistent with an increase in AMD1 on wounding, but there was no significant change in the levels of spermine or spermidine 6 hours or 12 hours post scratch (FIG. 4a). In AMD1-knockdown non-scratched cells, putrescine levels were 2.7-fold higher compared with the control cells. While spermidine levels showed no significant change following AMD1 knockdown, there was a 50% decrease in spermine levels (FIG. 4a). In scratched AMD1-knockdown cells, putrescine was no longer decreased but remained at similar levels to non-scratched cells. Spermine levels also remained low. This data demonstrates an AMD1-dependent shift in polyamine levels following scratch.

It is important to note that these measurements were performed on a population of cells containing both migrating cells at the wound edge and non-migrating cells further back from the wound edge. This is likely to lead to a dilution effect of the scratch-edge keratinocytes, potentially masking any changes that are localized at the wound edge. To address this, immunofluorescence studies were performed using an antibody specific to spermidine and spermine, but not to putrescine. In non-scratched cells, the levels of spermine and spermidine were low. Within 6 hours of scratching, increased fluorescence was seen predominantly in wound-edge keratinocytes in a pattern similar to AMD1 (FIG. 4b). This data shows that the levels of spermidine and spermine are increased at the wound edge where cells are migrating. To confirm this ex vivo, human histological wound samples were labelled with the same antibody. An increased spermidine/spermine staining in wound-edge keratinocytes could be observed 6 hours and 18 hour post wounding, compared to the time 0 hour wounded sections (FIG. 4c).

Polyamine Catabolism at the Wound Edge is Required for Cell Migration

Figure 5:
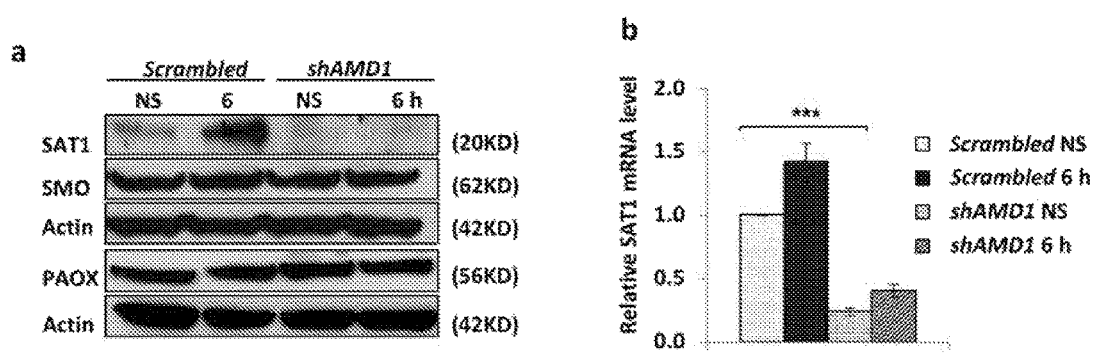
FIG. 5 shows data underlining that the polyamine catabolism at the wound edge is required for cell migration. (a,b) Western blot (a) and RT-PCR (b) showing SAT1 levels in non-scratched and 6 hours post-scratch samples from sh-scrambled and sh-AMD1 keratinocytes. SAT1 is upregulated following scratch in an AMD1-dependent manner. No change in SMO or PAOX protein expression was observed in scratched sh-scrambled and shAMD1 cells. (c) DCF-DA (10 μM) staining showing the production of DCF in response to ROS in scratched sh-scrambled and sh-AMD1 cells observed by fluorescence microscopy. Scale bar=100 μm. (d) Western blot showing decreased SAT1 protein levels in sh-scrambled and sh-SAT1 keratinocytes. (e) In vitro scratch assay on sh-scrambled and sh-SAT1 keratinocytes measured using the Incucyte Live Cell Analysis system showing impaired cell migration in sh-SAT1 cells. (f) Western blot of SAT1 and UPA in sh-scrambled and sh-SAT1 keratinocytes following scratch assay. Times shown are hours post scratch. (g,h) Immunofluorescence staining showing up-regulation uPAR (g) and uPAR (h) protein in scratched keratinocytes in sh-scrambled but not sh-SAT1 keratinocytes. Scale bar=25 μm NS denotes no scratch; Mean±standard error of three independent replicates are shown. *$P \leq 0.05$, $P \leq 0.01$, and *$P \leq 0.001$.
Figure 5:
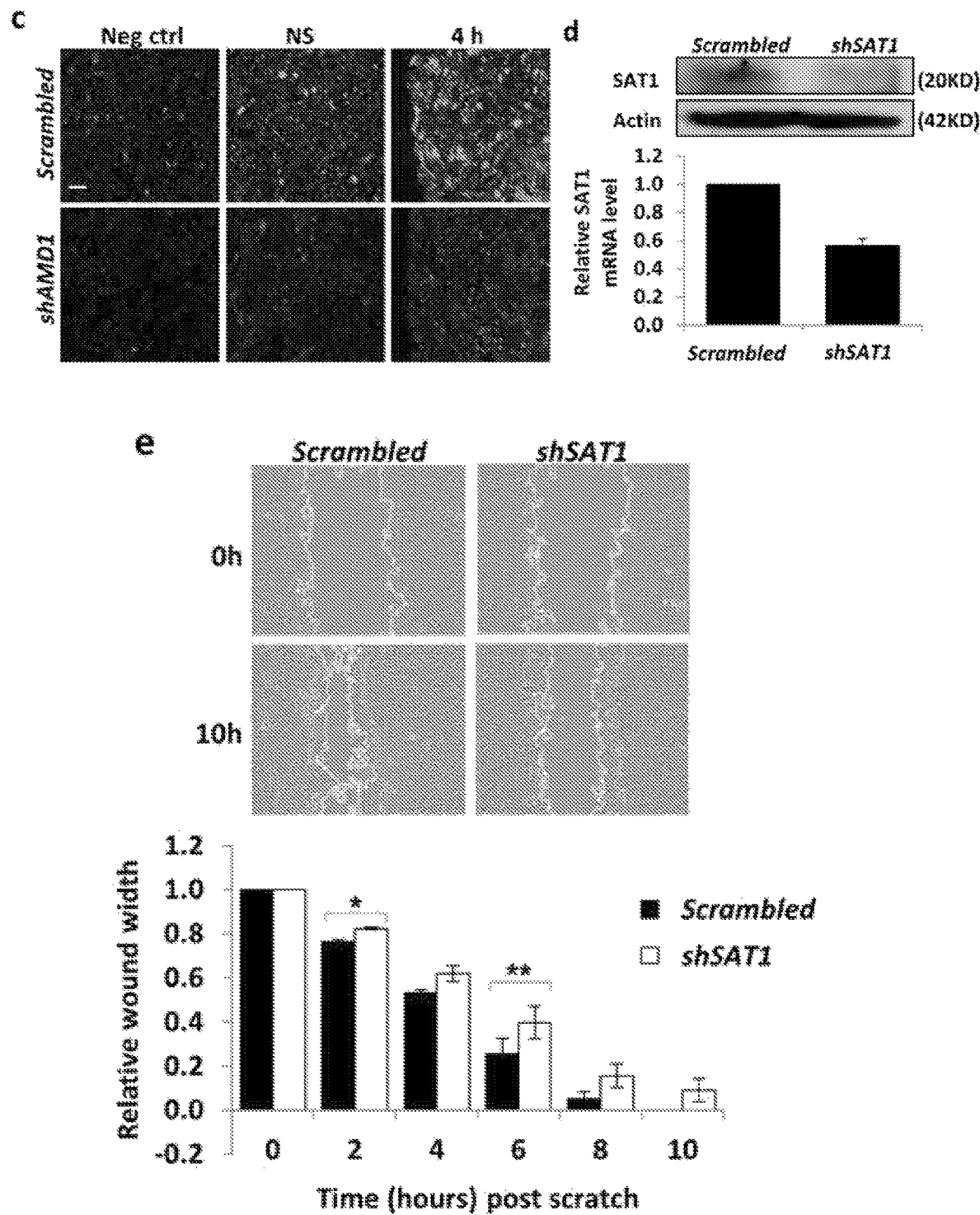
Figure 5:
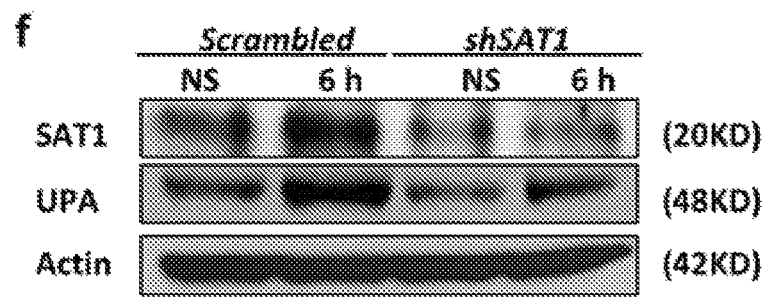
Figure 5:
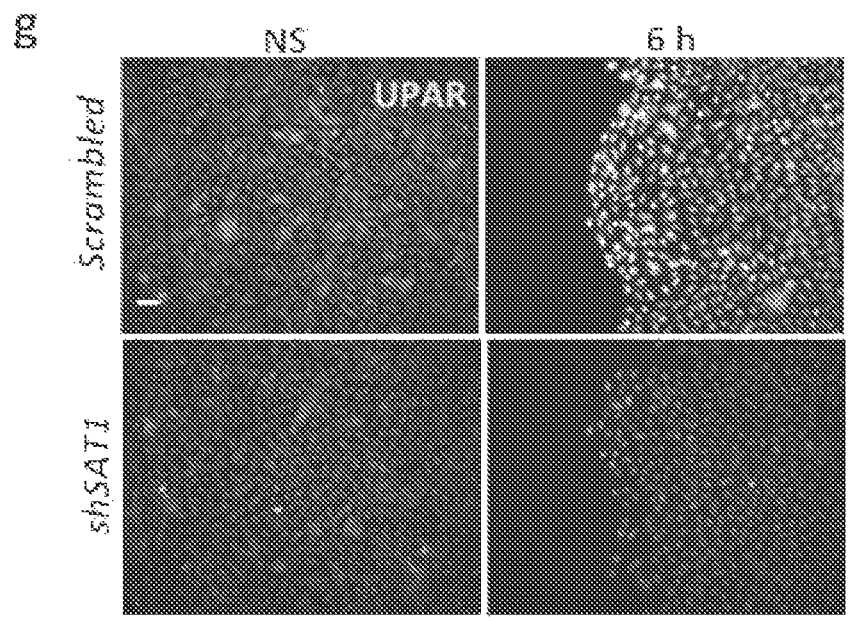
Figure 5:
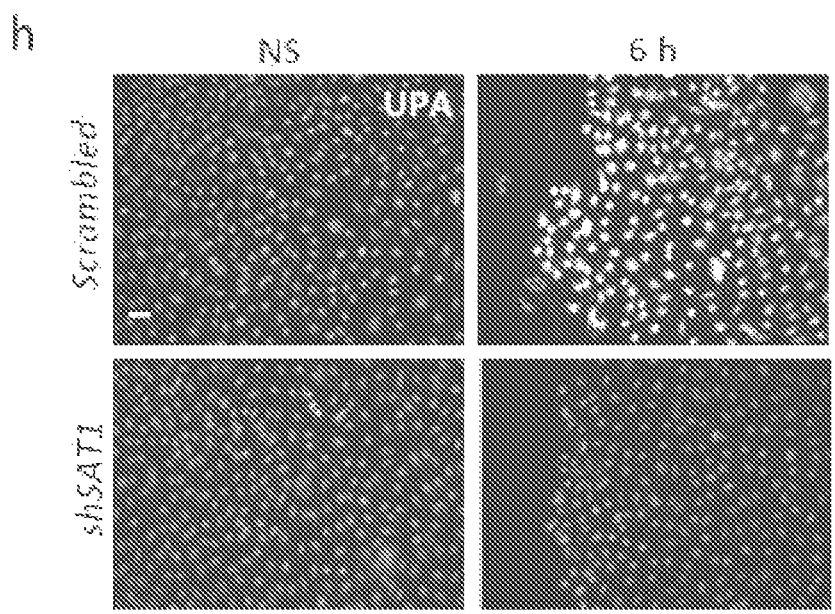

Polyamine homeostasis is regulated by feedback mechanisms generally involving the polyamines themselves affecting their rate of synthesis, catabolism, uptake and export. Polyamine catabolism is driven by two pathways: spermine oxidase (SMO) converts spermine back to spermidine while spermidine/spermine N1-acetyltransferase 1 (SAT1) acetylates spermine, which is then either exported from the cell or is oxidized by N1-acetylpolyamine oxidase (APAO) to spermidine. Spermidine can then be back-converted to putrescine through a similar SAT1/APAO-dependent reaction. To determine if the increased levels of spermine and spermidine in wound-edge keratinocytes could drive an increase in polyamine catabolism, the expression pattern of the two rate-limiting catabolic enzymes SAT1 and SMO were assessed using western blot. When keratinocytes were subjected to a scratch assay, the levels of SAT1 were up-regulated just 30 minutes post scratch and persisted for over 6 hours. There was no change in protein expression of SMO. The polyamine oxidase, PAOX, was also unchanged on wounding (FIG. 5a). SAT1 expression is thought to also be driven by increased spermine levels, so it was sought to determine if SAT1 up-regulation was dependent on AMD1. Analysis of SAT1 expression post scratch in AMD1-knockdown keratinocytes clearly demonstrated that the increase in SAT1 seen post scratch is dependent on AMD1 expression (FIG. 5a). While the increase in SAT1 protein expression was substantial post wounding, only a moderate increase in RNA expression was detected, suggesting that the increased protein levels observed are a consequence of increased translation or protein stability (FIG. 5b).

SAT1 catalyses the acetylation of spermidine and spermine, which are then either exported or oxidized by APAO to N-acetylaminopropanal, a lower order polyamine. This results in the release of $H_2O_2$, which has been shown in a number of different systems to be important in the wound healing process. To evaluate the levels of reactive oxygen species (ROS) on scratched cells, keratinocytes were pre-stained with DCFH-DA, a fluorescent ROS sensor, prior to scratch. The cells were visualized 6 hours post scratch to determine the level of cellular ROS. In scratched cells, fluorescence intensity was significantly increased, indicating an increase in ROS. This increase was abrogated in AMD1-knockdown cells following scratch (FIG. 5c), suggesting that on wounding, as modelled by a scratch assay, there is an increase in intracellular ROS that is at least partially dependent on AMD1 and is likely generated from the catabolism of polyamines.

Collectively, the data indicates that, on wounding, AMD1 is up-regulated and promotes an increase in spermine; this drives polyamine catabolism via SAT1 and a subsequent release of ROS ($H_2O_2$). To determine if polyamine catabolism is required for cell migration, SAT1 was knocked down using shRNA (FIG. 5d). Scratch assays on control and SAT1-knockdown cells confirmed that SAT1 up-regulation was abolished in the knockdown cells (FIG. 5f). Keratinocyte migration was significantly suppressed in shSAT1 keratinocytes following scratch (FIG. 5e), and up-regulation of the uPA-uPAR pathway was also significantly perturbed (FIG. 5f,g). Taken together, these results indicate that up-regulation of AMD1 on wounding drives the catabolism of spermidine/spermine by SAT1, which plays an essential role in keratinocyte migration.

Topical Application of Spermine Promotes/Accelerates Wound Repair in In Vitro and Ex-Vivo Human Skin Wounds To confirm a role for spermine and spermidine in regulating wound re-epithelialization, spermidine and spermine were added to human ex vivo wounds and examined the length of the migrating tongue after 72 hours. It was observed that addition of spermine or spermidine promoted a striking improvement in epithelial tongue migration (FIG. 6c), consistent with a previous in vitro model. Taken together, the data shows that, on epidermal wounding, AMD1 is rapidly up-regulated at the wound edge, which promotes a decrease in putrescine and an increase in spermine and spermidine, which in turn drives migration. This preliminary data clearly shows a role for polyamine regulator AMD1 in driving cell migration on wounding. The shift in polyamine ratios seen in wound edge keratinocytes is required to drive actin skeleton reorganization through the uPAR/uPA pathway to enable cell migration.

The data suggests that AMD1 induces signalling via the uPA-uPAR pathway to promote cell migration during wound repair. It was also shown that increased AMD1 levels are accompanied by a decrease in putrescine and an increase in spermine/spermidine levels at the wound edge. Given the observed change in polyamine levels on wounding, the influence of a topical application of putrescine, spermine, and spermine on cell migration of keratinocytes following a scratch assay (FIGS. 6a and 6b) was analysed. Putrescine treatment caused an inhibition of keratinocyte migration and a delay in closure of the scratch wound. The addition of spermine promoted scratch wound closure in the control cells. It was then attempted to rescue the AMD1-knockdown migration phenotype with supplementation of spermine and spermidine, while the replacement of spermine restored impaired cell migration in AMD1-knockdown cells.

It is shown herein that the polyamine regulator, AMD1, is a critical upstream regulator in the wound healing process. AMD1 is up-regulated at the wound edge within 10 min of wounding, initially spreading over 18 cells deep from the edge of the wound but then becoming restricted to wound edge keratinocytes where it is maintained at significantly elevated levels. Notably, the polyamine regulator, ODC1, does not show a similar pattern of up-regulation. That is to say that if in, for example a non-healing wound, AMD1 is not properly upregulated upon wounding, this would result in a high level of putrescine being present, which in turn can be detrimental to the healing process of the wound. A decrease in putrescine levels could then be brought about by, for example, addition of an ODC1 inhibitor and or the addition of dcAdomet, thereby targeting either the conversion of putrescine into spermidine or increasing the activity of AMD1 and/or increasing the concentration of products produced downstream from AMD1. As a result, there is a regulatory shift in the ratios of polyamines such that putrescine is decreased and spermine and spermidine are increased. Up-regulation of AMD1 is required for wound healing and functions in part to promote uPA/uPAR levels to enable reorganization of the actin cytoskeleton required for cell migration. Supplementation with spermine rescues the AMD1-knockdown phenotype and addition of spermine alone is sufficient to drive increased cell migration. AMD1 up-regulation is required to drive increased polyamine catabolism via SAT1 to support cell migration. It is indicated that polyamine catabolism releases significant quantities of intracellular $H_2O_2$, which behave as signalling molecules to promote cell migration.

The requirement for polyamines in normal cell function is well established. Levels of polyamine regulators and polyamines themselves are known to be significantly increased in cancer, and increased levels are seen in highly proliferative cells. However, less is known about their regulatory role where fluctuations in the levels and the ratios of the three polyamines might influence cellular behaviour and function. While ODC1 is the major rate-limiting enzyme for the synthesis of putrescine (which is then converted to spermidine and spermine), AMD1 is rate limiting for the conversion of putrescine to spermidine and spermine. As such, alterations in AMD1 levels will impact the ratio of putrescine to spermidine and spermine. Here, it is shown that keratinocytes at the epidermal wound edge rapidly up-regulate AMD1 on wounding. This occurs in the presence of only mild ODC1 up-regulation and therefore drives a shift in the ratio and levels of the three polyamines such that putrescine is decreased and spermine and spermidine are increased at the wound edge. It is thus indicated that wound-edge keratinocytes are sensitive to modulation of polyamine ratios within a physiological range for regulation of gene expression changes required for cell migration.

The data suggests that up-regulation of AMD1 not only drives an increase in spermine and spermidine at the wound edge but also activates polyamine catabolism with the consequent release of $H_2O_2$. $H_2O_2$ is known to be a critical signalling molecule during wound healing and it was demonstrated that high SAT1 is required for efficient cell migration and up-regulation of uPA/uPAR at the wound edge. $H_2O_2$ is known to be released following activation of DUOX in *Drosophila* wound models. The data shows that polyamine catabolism driven by increased AMD1 is an important source of intracellular $H_2O_2$ in the wound environment in the human epidermis. Increased $H_2O_2$ levels have been shown to regulate the expression of genes important for cell migration, indicating that the polyamine catabolism is a significant source of $H_2O_2$ following wounding. While increased polyamine catabolism and release of $H_2O_2$ has been shown to be detrimental during ischemia reperfusion injury in the heart, brain and kidney, it is believed, without being bound by theory, that the quantity of $H_2O_2$ generated at the wound edge would be sufficient to allow cell migration without being detrimental. In addition, wound-edge keratinocytes are known to up-regulate antioxidants to combat increased ROS at the wound site.

The up-regulation of AMD1 protein is detected within 10 min of wounding in wound-edge keratinocytes. Given the rapid up-regulation seen by immunofluorescence at the wound edge and the more significant up-regulation seen at 2 to 4 hours post wounding by Western blot and qRT-PCR, it is thought that the initial burst in AMD1 protein in wound-edge keratinocytes is a result of increased translation or protein stabilization. This is then further enhanced by promotion of transcription detectable 1 to 2 hours post wounding by PCR. AMD1 is known to be regulated at transcriptional, translational, and post-translational levels and it is likely to be a combination of regulatory events that function to promote AMD1 protein at the wound edge. One of the earliest events detected post-wounding is the release of an intracellular calcium wave that travels from the wound edge away from the wound to neighbouring keratinocytes. Addition of thapsigargin and EDTA to remove intra- and extracellular calcium completely abrogates AMD1 protein up-regulation. Thus, up-regulation of AMD1 is considered to be a very early downstream effector of calcium signalling required to enable wound closure. AMD1 then functions to drive gene expression changes through increased spermine/spermidine and increased $H_2O_2$.

Migration of keratinocytes at the wound edge is supported by an increase in keratinocyte proliferation behind the migrating cells to provide sufficient cells to cover the wound. It has been shown that ODC1 is up-regulated at the wound edge and this likely drives an increase in all three polyamines to drive increased proliferation. A strong AMD1 up-regulation was seen to be restricted to the keratinocytes 5 to 6 cells deep at the wound edge, where the up-regulation drives a shift in polyamine ratios. The data indicates that high spermine and spermidine along with decreased putrescine is required specifically for leading-edge cells to migrate across the wound. A characteristic of non-healing wounds is a failure of keratinocyte migration with increased proliferation at the wound edge. It is thought that the regulation of polyamines seen in normal wounds is defective in non-healing wounds, and that the correct balance in the ratios and levels of putrescine, spermidine, and spermine is required for efficient wound closure.

Materials and Methods
Cell Culture

Human immortalized keratinocytes (Dickson et al., 2000), N/TERT-1 were obtained and cultured in keratinocyte serum-free media (K-SFM; Life Technologies; Thermo Fisher Scientific) supplemented with 25 µg/ml bovine pituitary extract (BPE), 0.2 ng/ml epidermal growth factor (EGF), and 0.3 mM $CaCl_2$, as previously described (Rheinwald et al., 2002). To culture cells to 100% confluence for scratch assays, N/TERT-1 cells were first cultured to 50% confluence in supplemented K-SFM growth medium and then switched to a media with a 1:1 ratio mixture of supplemented K-SFM and DF-K (a mixture of calcium free, glutamine free DMEM (Hyclone; GE Healthcare) with Ham's F-12/GlutaMAX (Gibco; Life Technologies; Thermo Fisher Scientific) at 1:1 (vol/vol) supplemented with 5 µg/ml BPE, 0.2 ng/ml EGF, and 1.5 mM L-glutamine (Life Technologies; Thermo Fisher Scientific)) until 100% confluent. Human HEK293T cells (Dharmacon; GE Healthcare) were used for lentiviral production as the packaging cell line and cultured in high glucose DMEM (Hyclone; GE Healthcare) with 10% fetal calf serum. All cells were grown in a humidified incubator with 5% CO2 at 37° C.

Lentiviral Knockdown shRNAs against AMD1 and SAT1 were purchased from Thermo Fisher Scientific. Target sequences for AMD1 silencing are 5'-AGACTTCTACAACTTTCCT-3' (SEQ ID NO. 1) and 5'-TTAATAGAACAGTCCTAGA-3' (SEQ ID NO. 2). Target sequences for SAT1 silencing are 5'-TATATTAAGATCACACCAC-3' (SEQ ID NO. 3) and 5'-TTATAGAAGTTGATGGATG-3' (SEQ ID NO. 4). Lentivirus was generated according to the manufacturer's protocol (Thermo Fisher Scientific). Stable cell lines were generated by selecting virally transduced cells for 7-10 days with 2 µg/ml puromycin (Sigma-Aldrich). All experiments were performed on cells under 10 passages from transfection.

In Vitro Scratch Cell Migration Assay

Confluent keratinocytes on ImageLock 96-well microplates (Essen BioScience, Inc) were scratched using a 96-pin wound maker (Essen BioScience, Inc) to create homogeneous, 700-800-µm wide scratch wounds in cell monolayers. Scratched cells were imaged using a real-time cell imaging system, IncuCyte, (Essen BioScience, Inc) to monitor cell migration. Putrescine, spermidine, or spermine (5 µM, Sigma-Aldrich) were added to cells and incubated for 48 h prior to scratch. For analysis of protein and RNA expression in migrating cells, keratinocytes were cultured to full confluency in a 6-well culture dish (Corning Costar) and scratched with the large end of a 1-mL pipette tip. At specific time points, the cells were either harvested in lysis buffer (150 mM sodium chloride, 1% (v/v) Triton X-100, 0.5% sodium deoxycholate, 1% (v/v) sodium dodecyl sulfate, 50 mM Tris-HCl, 1% (v/v) Nonidet P-40 (NP-40), 0.1 mM phenylmethylsulfonyl fluoride (PMSF), 5 mM EDTA, and 1% (v/v) protease and phosphatase inhibitor cocktail) for western blot or Trizol reagent (Life Technologies; Thermo Fisher Scientific) for RNA analysis.

Calcium ($Ca^{2+}$) Wave Imaging

Keratinocytes were seeded in glass-bottom 35-mm² dishes and cultured to full confluency in cell culture media. To deplete intracellular and extracellular $Ca^{2+}$ sources, cells were treated with 1 µM thapsigargin (Tg) (Sigma-Aldrich) for 24 hours and 2 mM ethylene glycol tetraacetic acid (EGTA, Sigma-Aldrich) for 1 hour prior to scratch. For $Ca^{2+}$ flux imaging, cells were incubated with Fluo-4,AM (Life Technologies; Thermo Fisher Scientific) and imaged with an automated confocal microscope (Spinning disk 3D-FRAP; Nikon Ti) at 0.2 second intervals for 5 minutes. Image analysis was performed using ImageJ software.

Human Wound Biopsies

Human skin samples were sourced from Dr T. C. Lim at the Yong Loo Lin School of Medicine, National University of Singapore. Written consent from participants was obtained in all cases. The study was done in accordance with the declaration of Helsinki and was approved by a local scientific ethics review board. The skin was further dissected into 6-mm cubes or circles. Excisional skin wounds of approximately 3 to 4 mm were made with surgical scissors. The ex vivo wounded skin explants were cultured at the air-liquid interface and treated topically with 500 µM of putrescine, spermidine, spermine or 1× phosphate-buffered saline (PBS) every 24 hours for 3 days. Non-wounded skin, day 0- and day 3-wounded biopsies were bisected, with half snap-frozen in Optimal Cutting Temperature Compound (OCT) and the other half fixed in 10% buffered formalin saline and embedded in paraffin for histological analysis.

Histology, Immunohistochemistry, and Immunofluorescence

Histological sections were prepared from wound tissue embedded in paraffin or snap-frozen in OCT. 7 µm thick sections were stained with hematoxylin and eosin For immunofluorescence, sections or in vitro scratched cells on cover slips were incubated with primary antibodies against AMD1, SAT1 (sc-390037; sc-67159; Santa Cruz Biotechnology, Inc), Spermine and Spermidine (Ab26975; Abcam) uPA and uPAR (GTX89445; GTX59605; GeneTex, Inc), followed by appropriate Alexa Fluor 488 or 594 conjugated secondary antibodies (Life Technologies; Thermo Fisher Scientific) and counterstained with Hoechst 33342 (Molecular Probes). To visualise F-actin filaments, the cells were incubated with Alexa Fluor 568 labelled phalloidin (A12380; Life Technologies; Thermo Fisher Scientific) and counterstained with Hoechst 33342. Images were acquired using a fluorescence microscope (Zeiss AxioImager Z1; Carl Zeiss). All images were taken at room temperature with a Texas red or GFP filter. Image analysis was performed using Zeiss image analysis software, ZEN Pro.

Quantitative Real-Time PCR

Total RNA was isolated from keratinocytes using the RNeasy kit (QIAGEN). One microgram of total RNA was reverse transcribed to cDNA using the RevertAid reverse transcription kit (Thermo Fisher Scientific) according to the manufacturer's instruction. Luminaris Colour HiGreen Hi ROX master mix (Thermo Fisher Scientific) was used with transcript-specific primers for qRT-PCR on an ABI PRISM 7900 sequence detection system. Primers were either purchased from Integrated DNA Technologies (IDT) or designed and validated. CT values were normalized to the GAPDH or ribosomal protein LPO or L13A mRNA.

Western Blot

Ninety micrograms of protein from each sample was resolved on a 4-12% Bis-Tris gel (NuPAGE) and transferred onto nitrocellulose membranes (Amersham; GE Healthcare). The membranes were incubated overnight with primary antibodies against FLG, INV, and GAPDH (ab3137; ab53112; ab9484; Abcam), AMD1, ODC1, SMS1 and SAT1 (sc-390037; sc-21515; sc-376294; sc-67159; Santa Cruz Biotechnology, Inc), uPAR and uPA (GTX59605 and GTX89445; GeneTex, Inc), PAOX and SMO (PAS-25758; PA-18588; Pierce; Thermo Fisher Scientific) and β-actin (A5441; Sigma-Aldrich) after blocking with 5% skim nonfat milk (ChemCruz; Santa Cruz Biotechnology, Inc) in TBS-T (0.1% Tween-20 (Sigma-Aldrich) in 1×TBS (0.1 M NaCl, 0.1 M Tris pH 7.4 in ddH$_2$O) The samples were then incubated with HRP-labelled anti-rabbit, anti-mouse, or anti-goat IgG (Santa Cruz Biotechnology, Inc) and immunoreactive bands were detected with enhanced chemiluminescent substrate (Thermo Fisher Scientific).

Measurement of Polyamine Levels

High-performance liquid chromatography (HPLC) was used to measure the levels of polyamines as previously described (Igarashi, K., Kashiwagi, K., Hamasaki, H., Miura, A., Kakegawa, T., Hirose, S., and Matsuzaki, S. (1986). Formation of a compensatory polyamine by *Escherichia coli* polyamine-requiring mutants during growth in the absence of polyamines. J Bacteriol 166, 128-134).

Cellular Reactive Oxygen Species (ROS) Detection

Cells were incubated with 20 µM 2',7'-dichloro-dihydrofluorescein diacetate (DCFH-DA) (Abcam) for 45 minutes at 37° C. in the dark. Cell monolayers were scratched with the top of a 1-ml pipette tip to create a single scratch. After 6 hours, cells were rinsed once with 1×PBS. Oxidized 2',7'-dichloro-fluorescein (DCF) was detected by fluorescence microscopy (Zeiss AxioImager Z1; Carl Zeiss) at maximum excitation and emission spectra of 495 nm and 529 nm, respectively.

Statistical Analysis

All data is presented as mean±SE. Two-tailed Student's t test was used to determine the significance between two groups. P-values lower than 0.05 (p<0.05) were considered to be statistically significant.

What is claimed is:

1. A method of promoting re-epithelialisation of a wound or for treating a wound, the method comprising administering a pharmaceutically effective amount of a composition to a subject in need thereof, wherein the composition comprises spermine, spermidine, or a combination thereof.

2. A method of treating a non-healing wound in a subject, wherein the method comprises:
   determining the level of at least one polycationic aliphatic amine in a sample obtained from the wound of the subject;
   comparing the levels of the at least one polycationic aliphatic amine with the levels of the same polycationic aliphatic amine found in a sample obtained from a subject without wound;
   wherein, upon comparison, an increased level of the at least one polycationic aliphatic amine in the wound sample is indicative of a non-healing environment and thus a non-healing wound; wherein the at least one polycationic aliphatic amine is putrescine;
   wherein the method further comprises determining the level of a second polycationic aliphatic amine in the same sample as previously obtained from the wound of a subject and comparing the level determined for the second polycationic aliphatic amine to the level of the same second polycationic aliphatic amine in the sample obtained from a subject without wound, wherein an increased level of the second polycationic aliphatic amine is indicative of progression of wound healing, and wherein decreased level of the second polycationic aliphatic amine is indicative of no progression or regression of wound healing; wherein the second polycationic aliphatic amine is spermine or spermidine, or a combination thereof,
   administering a pharmaceutically effective amount of a composition to the subject suffering from said non-healing wound; wherein the composition comprises spermine, spermidine, or a combination thereof.

3. The method of claim 1 wherein the wound is a non-healing wound or a slow-healing wound.

4. The method of claim 1, wherein the wound is an epithelial wound.

5. The method of claim 1, wherein the wound is cutaneous.

6. The method of claim 1, wherein the sample is taken from the group consisting of wound exudate, wound edge and wound centre.

7. The method of claim 1, wherein the subject suffers from an underlying condition or disease, or wherein the subject is undergoing further treatment.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Target sequence for AMD1 silencing

<400> SEQUENCE: 1
agacttctac aactttcct                                              19

<210> SEQ ID NO 2
<211> LENGTH: 19
<212> TYPE: DNA
<213> ORGANISM: Artificial Sequence
<220> FEATURE:
<223> OTHER INFORMATION: Target sequence for AMD1 silencing

<400> SEQUENCE: 2

```
ttaatagaac agtcctaga                                                    19

<210> SEQ ID NO 3
<211> LENGTH: 19
<212> TYPE: DNA
<213> ORGANISM: Artificial Sequence
<220> FEATURE:
<223> OTHER INFORMATION: Target sequence for SAT1 silencing

<400> SEQUENCE: 3
tatattaaga tcacaccac                                                    19

<210> SEQ ID NO 4
<211> LENGTH: 19
<212> TYPE: DNA
<213> ORGANISM: Artificial Sequence
<220> FEATURE:
<223> OTHER INFORMATION: Target sequence for SAT1 silencing

<400> SEQUENCE: 4
ttatagaagt tgatggatg                                                    19
```